US009131965B2

(12) United States Patent
Prewett et al.

(10) Patent No.: US 9,131,965 B2
(45) Date of Patent: Sep. 15, 2015

(54) SWELLABLE INTERSPINOUS STABILIZATION IMPLANT

(75) Inventors: Ann Prewett, Bloomfield Hills, MI (US); Alan Chen, Cranbury, NJ (US); Frederick H. Hardenbrook, Egg Harbor Township, NJ (US)

(73) Assignees: REPLICATION MEDICAL INC., Cranbury, NJ (US); HYDRA MEDICAL LLC, Bloomfield Hills, MI (US)

( * ) Notice: Subject to any disclaimer, the term of this patent is extended or adjusted under 35 U.S.C. 154(b) by 878 days.

(21) Appl. No.: 12/580,101

(22) Filed: Oct. 15, 2009

(65) Prior Publication Data

US 2010/0100183 A1    Apr. 22, 2010

Related U.S. Application Data

(60) Provisional application No. 61/105,554, filed on Oct. 15, 2008, provisional application No. 61/122,897, filed on Dec. 16, 2008.

(51) Int. Cl.
*A61B 17/70* (2006.01)
*A61F 2/44* (2006.01)
*A61B 17/00* (2006.01)

(52) U.S. Cl.
CPC ......... *A61B 17/7065* (2013.01); *A61B 17/7068* (2013.01); *A61F 2/4405* (2013.01); *A61B 2017/00871* (2013.01); *A61B 2017/00898* (2013.01); *A61F 2/441* (2013.01)

(58) Field of Classification Search
CPC ........... A61B 17/7065; A61B 17/7068; A61B 2017/00871; A61B 2017/00898; A61F 2/4405; A61F 2/441
USPC .................... 623/17.11–17.16; 606/246–279
See application file for complete search history.

(56) References Cited

U.S. PATENT DOCUMENTS 4,107,121 A    8/1978    Stoy
4,331,783 A    5/1982    Stoy
(Continued)

FOREIGN PATENT DOCUMENTS

WO    WO 2006/136938 A1    12/2006
WO    WO 2008068162 A1 *  6/2008

OTHER PUBLICATIONS

International Search Report and Written Opinion of the International Searching Authority, PCT/US2009/060896, date of completion is Dec. 18, 2009; 10 pages.

*Primary Examiner* — Jerry Cumberledge
*Assistant Examiner* — Nicholas Plionis
(74) *Attorney, Agent, or Firm* — Carter, DeLuca, Farrell & Schmidt, LLP

(57) ABSTRACT

A swellable, resilient interspinous implant is provided that includes a swellable polymeric medium, said polymeric medium being dispersed throughout the implant, the implant being dimensioned and configured to fit between two spinous processes of two adjacent vertebrae and buttress the space between the two adjacent vertebrae. In embodiments, the implant has a first configuration of reduced size such that it can be inserted into the patient in a minimally invasive manner. Once inserted to an application point within the patient, the implant expands in size to dynamically maintain the adjacent spinous processes in beneficial alignment. Also provided is a method of making a swellable, resilient interspinous implant as described herein. Also provided is a method of treating a degenerative condition of a spine which includes creating an incision and inserting, through the incision, between two spinous processes of two adjacent vertebrae, a swellable, resilient interspinous implant as described herein.

59 Claims, 13 Drawing Sheets

(56) References Cited

U.S. PATENT DOCUMENTS

| | | |
|---|---|---|
| 4,337,327 A | 6/1982 | Stoy |
| 4,369,294 A | 1/1983 | Stoy |
| 4,370,451 A | 1/1983 | Stoy |
| 4,379,874 A | 4/1983 | Stoy |
| 4,420,589 A | 12/1983 | Stoy |
| 4,943,618 A | 7/1990 | Stoy et al. |
| 5,252,692 A | 10/1993 | Lovy et al. |
| 5,496,318 A | 3/1996 | Howland et al. |
| 5,571,189 A | 11/1996 | Kuslich |
| 5,609,634 A | 3/1997 | Voydeville |
| 5,645,599 A | 7/1997 | Samani |
| 5,836,948 A | 11/1998 | Zucherman et al. |
| 6,074,390 A | 6/2000 | Zucherman et al. |
| 6,099,531 A | 8/2000 | Bonutti |
| 6,232,406 B1 | 5/2001 | Stoy |
| 6,238,397 B1 | 5/2001 | Zucherman et al. |
| 6,264,695 B1 | 7/2001 | Stoy |
| 6,440,169 B1 | 8/2002 | Elberg et al. |
| 6,626,944 B1 | 9/2003 | Taylor |
| 6,699,247 B2 | 3/2004 | Zucherman et al. |
| 6,726,721 B2 | 4/2004 | Stoy et al. |
| 6,733,534 B2 | 5/2004 | Sherman |
| 6,796,983 B1 | 9/2004 | Zucherman et al. |
| 7,029,473 B2 | 4/2006 | Zucherman et al. |
| 7,101,375 B2 | 9/2006 | Zucherman et al. |
| 7,189,234 B2 | 3/2007 | Zucherman et al. |
| 7,306,628 B2 | 12/2007 | Zucherman et al. |
| 7,361,196 B2 | 4/2008 | Fallin et al. |
| 2005/0245937 A1* | 11/2005 | Winslow .................. 606/90 |
| 2006/0058790 A1* | 3/2006 | Carl et al. .................. 606/61 |
| 2006/0084983 A1* | 4/2006 | Kim .................. 606/61 |
| 2006/0136065 A1 | 6/2006 | Gontarz et al. |
| 2006/0235387 A1* | 10/2006 | Peterman .................. 606/61 |
| 2006/0241601 A1* | 10/2006 | Trautwein et al. .................. 606/61 |
| 2006/0247623 A1* | 11/2006 | Anderson et al. .................. 606/61 |
| 2006/0264938 A1 | 11/2006 | Zucherman et al. |
| 2006/0265066 A1 | 11/2006 | Zucherman et al. |
| 2006/0271049 A1 | 11/2006 | Zucherman et al. |
| 2006/0293662 A1* | 12/2006 | Boyer et al. .................. 606/61 |
| 2007/0043362 A1 | 2/2007 | Malandain et al. |
| 2007/0135922 A1* | 6/2007 | Trieu .................. 623/17.12 |
| 2007/0191956 A1 | 8/2007 | Prewett et al. |
| 2007/0270823 A1* | 11/2007 | Trieu et al. .................. 606/61 |
| 2007/0276369 A1 | 11/2007 | Allard et al. |
| 2007/0276493 A1* | 11/2007 | Malandain et al. .................. 623/17.11 |
| 2008/0249604 A1* | 10/2008 | Donovan et al. .................. 623/1.15 |
| 2008/0300686 A1* | 12/2008 | Khoo .................. 623/17.11 |

* cited by examiner

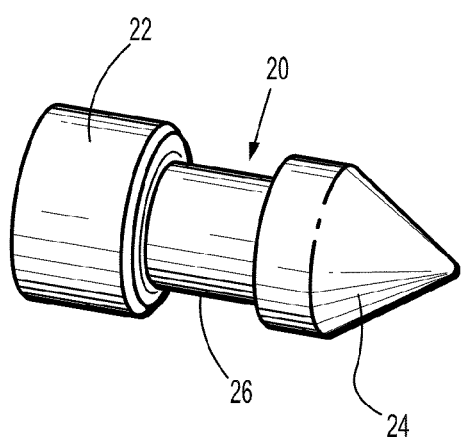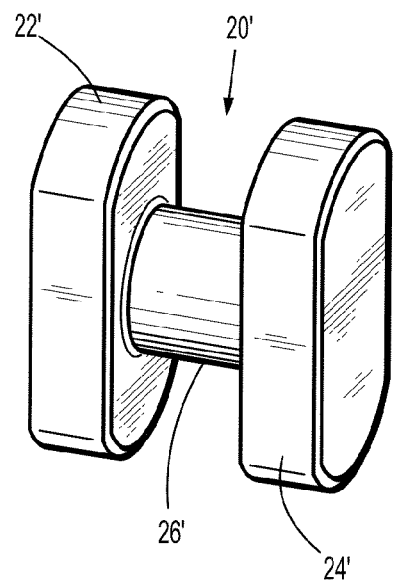
FIG. 3     FIG. 4

SWELLABLE INTERSPINOUS STABILIZATION IMPLANT

CROSS-REFERENCE TO RELATED APPLICATIONS

This application claims priority of U.S. Provisional Application Ser. No. 61/105,554, filed Oct. 15, 2008 and U.S. Provisional Application Ser. No. 61/122,897, filed Dec. 16, 2008 and both are incorporated herein by reference in their entireties.

BACKGROUND

1. Field of the Invention

Dynamic stabilization of the spine.

2. Description of Related Art

Physical discomfort from degenerative conditions of the spine such as disc disease, spinal stenosis, and spondylolisthesis affects a large segment of the population. Symptoms are related to compression of spinal nerves or nerve roots and may include intermittent neurogenic claudication, pain in back or legs, numbness, weakness and loss of balance. Conservative treatment may include rest, physical therapy, bracing, anti-inflammatory medications, analgesics, local anesthetic blocks and epidural steroid injections.

Treatment by spinal fusion is frequently offered to patients who suffer from these conditions. However, fused vertebrae have been associated with loss of mobility and deterioration of adjacent discal architecture due to increased strain and forces at such discs. Dynamic spinal stabililization of the spine is a treatment modality intended to overcome such deficiencies. Dynamic stabilization allows adjacent vertebrae to be stabilized through the use of, e.g., articulating structures, compressible structures and the like, to allow relative movement of adjacent vertebrae which are supported by such structures. In this manner, the aforementioned disadvantages of rigid fusion are avoided.

Dynamic stabilization typically involves rigid fastening of a dynamic stabilization implant (DSI) to one or more vertebrae using devices such as pedicle screws. In addition, DSIs are typically made of hard metals or plastics to provide adequate support between adjacent vertebrae under loaded conditions. In the case of rigid attachment, the point of attachment is usually subject to the brunt of the stress caused by normal movement. Moreover, such rigid attachment is a traumatic event for the bone itself. Use of rigid materials to construct the implant also provides for concentration of forces at the surface of the implant and can cause erosion of natural surfaces that contact the implant.

Surgical decompression with or without fusion is the standard surgical treatment for patients with moderate to severe lumbar spinal stenosis. Cervical, thoracic, and/or lumbar interspinous process decompression (IPD), also known as interspinous distraction or posterior spinal distraction, is a form of dynamic stabilization that has been proposed as a minimally invasive alternative to laminectomy and fusion. In IPD an interspinous distraction implant is inserted between the spinous processes through a small (e.g., 4-8 cm) incision. The device is intended to restrict painful motion while enabling otherwise normal motion. The implant theoretically enlarges the neural foramen, decompresses the cauda equina and acts as a spacer between the spinous processes to maintain the flexion of the spinal interspace.

There is continuing need for improved methods and devices for stabilizing compromised spinal architecture.

SUMMARY

A swellable, resilient self-retaining interspinous implant is provided that includes a swellable polymeric medium, said polymeric medium being dispersed throughout the implant, the implant being dimensioned and configured to fit between two spinous processes of two adjacent vertebrae and buttress the space between the two adjacent vertebrae. In embodiments, the implant has a first configuration of reduced size such that it can be inserted into the patient in a minimally invasive manner. Once inserted to an application point within the patient, the implant expands in size to dynamically maintain the adjacent spinous processes in beneficial alignment. Two oppositely disposed retaining members, which are connected by a centrally disposed cross member, act to stabilize the implant by engaging the spinous processes of adjacent vertebrae. In embodiments, the oppositely disposed retaining members have at least a portion thereof canted inwardly toward one another. The swellable polymeric medium may be a fluid absorbing polymer, e.g., a hydrogel. The swellable polymeric medium may also be a substantially non-fluid absorbing elastic polymer. In embodiments, the implant is capable of expanding from a compact, substantially dehydrated configuration to an expanded hydrated configuration. In embodiments, the implant is configured to transform from a first configuration to a second configuration, the first configuration having a smaller cross-section than the second configuration. In embodiments, the implant is capable of undergoing anisotropic expansion from the first configuration to the second configuration. In embodiments, the implant is capable of undergoing isotropic expansion from the first configuration to the second configuration.

In embodiments, the implant includes an interiorly disposed support member. In embodiments, at least a portion of the interiorly disposed support member extends beyond the periphery of the implant. In embodiments the support member is made of flexible fibers. The flexible fibers may be made, e.g., from natural or synthetic polymers or metal. In embodiments, the support member is fabric selected from the group consisting of mesh, woven fabric and nonwoven fabric made of flexible fibers. In embodiments, the support member is a braided three-dimensional support member made of flexible fibers. In embodiments, the interstices of the braided three-dimensional support member are filled with the polymeric medium. In embodiments, the support member is a flexible foil made from metal or a polymer. In embodiments, at least a portion of the implant includes a wear reducing surface adapted and configured to contact bone. In embodiments, a radiopaque material may be included in or around the implant.

Also provided is a method of making a swellable, resilient, self-retaining interspinous implant which includes providing a mold defining a cavity adapted and configured to approximate at least a portion of the space between two spinous processes of two adjacent vertebrae, providing a liquid polymer, filling the mold with the liquid polymer and coagulating the liquid polymer to form a swellable, resilient, self-retaining interspinous implant adapted and configured to fit between two spinous processes of two adjacent vertebrae and buttress the space between the two adjacent vertebrae. In embodiments, the mold cavity has first and second end portions and a center portion, the first and second end portions being larger than the center portion. In embodiments, the mold cavity defines a dumbbell shape. In embodiments, the mold cavity defines an hourglass shape. In embodiments, the method further includes providing a support member, positioning the support member in said mold such that the liquid polymer can at least partially cover the support member, and coagulating the liquid polymer. In embodiments, the support member is a braided three-dimensional member configured and dimensioned to have a shape consistent with the mold cavity. In embodiments the liquid polymer is a fluid absorbing polymer. The fluid absorbing polymer can be a hydrogel. In embodiments, a support member, e.g., a braided three-dimensional support member is placed within a mold cavity which has dimensions greater than the braided three-dimensional support member to allow the liquid fluid absorbing polymer to be absorbed into and saturate the braided three-dimensional support member and to encapsulate the braided three-dimensional support member with a layer of fluid absorbing polymer. In embodiments, the interspinous implant is dehydrated to reduce the dimensions of the implant.

Also provided is a method of treating a degenerative condition of a spine which includes creating an incision and inserting, through the incision, between two spinous processes of two adjacent vertebrae, a swellable, self-retaining resilient interspinous implant made of a polymeric medium, said polymeric medium being dispersed throughout the implant, the implant being dimensioned and configured to fit between two spinous processes of two adjacent vertebrae to buttress the space between the two adjacent vertebrae. In embodiments, the interspinous implant is secured to a guide wire and implanted percutaneously. In embodiments, the interspinous implant includes an internal shaft coaxial with the longitudinal axis of the implant for receiving the guide wire. In embodiments, the implant has a first configuration of reduced size such that it can be inserted into the patient in a minimally invasive manner. In embodiments, the implant is capable of expanding from a compact, substantially dehydrated configuration to an expanded hydrated configuration. In embodiments, the implant is configured to transform from a first configuration to a second configuration, the first configuration having a smaller cross-section than the second configuration. Once inserted to an application point within the patient, the implant expands in size to dynamically maintain the adjacent spinous processes in beneficial alignment.

BRIEF DESCRIPTION OF THE DRAWINGS

FIG. 3 is a perspective view of an embodiment of an interspinous implant in a compacted state.

FIG. 4 is a perspective view of an embodiment of an interspinous implant shown in FIG. 3 in an expanded state.

DETAILED DESCRIPTION OF PREFERRED EMBODIMENTS

Figure 1:
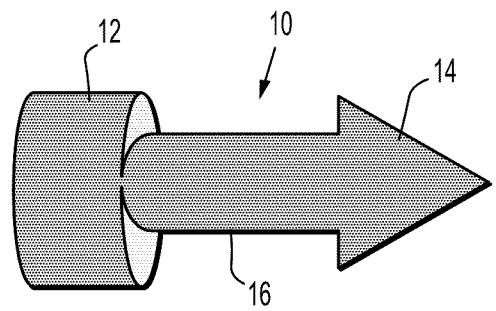
FIG. 1 is a dimensional view of an embodiment of an interspinous implant in a compacted state.

A swellable, resilient, self-retaining interspinous implant according to the present disclosure is uniquely suited for minimally invasive interspinous implantation by virtue of its ability to achieve an optimum implantable substantially reduced configuration and further ability to expand anisotropically or isotropically to an expanded configuration which is adapted and configured to fit between, and secure, two spinous processes of two adjacent vertebrae and buttress the space between the two adjacent vertebrae. The techniques described herein provide an interspinous implant which, in the reduced, or compacted, configuration, has a relatively narrow cross-section and is elongate in the longitudinal direction so that, in embodiments, an overall substantially rod-shaped configuration is manifest. In embodiments, the rod-shaped configuration is, e.g., arrow-shaped. See, e.g., FIGS. 1, 3 and 6. The reduced configuration fits through a minimally invasive incision as a result of its small cross-section and stable structure. After implantation, the interspinous implant has a surprising capacity to expand anisotropically or isotropically from the small cross-sectional configuration into an expanded dumbbell-like or hourglass-like configuration which fills at least a majority of the interspinous space as it expands and also secures itself in place (i.e., self-retaining) by frictionally engaging the vertebral processes.

In embodiments, the unconstricted volume of the interspinous implant, when expanded (also referred to herein as the second configuration), is slightly greater than the interspinous space between two adjacent vertebrae when the spine is in a neutral position such that, in situ, the implant is slightly compressed when the spine is in the neutral position. In this manner, the interspinous implant exerts positive pressure against the vertebrae to alleviate compression during extension, effectively acting as an extension stop while allowing freedom of spinal flexion. In addition, maintaining pressure within the interspinous space secures the interspinous implant in place by virtue of the friction created thereby.

In particular, the interspinous implant has a first retainer end portion, and oppositely disposed second retainer end portion and an interconnecting central portion. The central portion has a smaller cross-section than either of the end portions. As mentioned above, in embodiments, e.g., the interspinous implant has an hourglass shape and in other embodiments, e.g., the interspinous implant has a dumbbell shape. The central portion is dimensioned and configured to be disposed between the bone architecture defining the interspinous space between two adjacent vertebrae and to exert positive pressure against extension. The oppositely disposed first and second end retainer portions are dimensioned and configured to engage the spinous processes of adjacent vertebrae at their respective outer sagittal faces and anchor the central portion of the interspinous implant in place against the lamina and respective vertebral bodies. The inward facing surfaces of the two respective retainer end portions frictionally engage the outer sagittal faces of the spinous processes.

Figure 2:
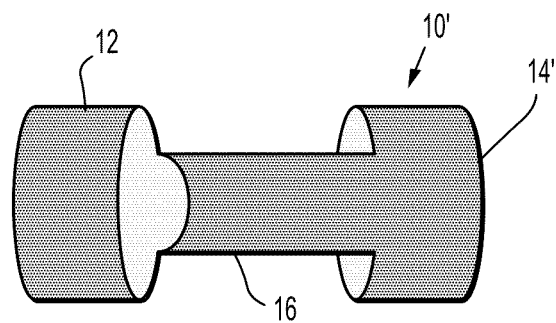
FIG. 2 is a dimensional view of the interspinous implant shown in FIG. 1 in an expanded state.

An example of an interspinous implant 10 and 10' is shown in FIGS. 1 and 2. A partially compacted interspinous implant 10 has a first retainer end portion 12, an oppositely disposed compacted second retainer end portion 14 having an arrow-head shape and an interconnecting member 16. As described more fully below, the arrow head shape is imparted using shape memory techniques which, upon expansion of the compacted portion, assumes a desired second configuration. FIG. 2 depicts a interspinous implant 10' of the type exemplified in FIG. 1 in an expanded state. Second retainer end portion 14 expands into a disc shape 14' which corresponds to the shape of the first retainer end portion 12. Another example of an interspinous implant is shown in FIGS. 3 and 4. A compacted interspinous implant 20 has a first retainer end portion 22 having a disc shape, an oppositely disposed compacted second retainer end portion 24 having an arrow-head shape and an interconnecting member 26 as shown in FIG. 3. The expanded interspinous implant 20' is shown in FIG. 4. The first retainer end portion 22 expands into a oblong rectangular shape 22' due to shape memory characteristics of the swellable polymer. The second retainer end portion 24 expands from the arrow-head shape into a oblong rectangular shape 24' corresponding to the shape of first retainer end portion 22 due to shape memory characteristics of the swellable polymer. The interconnecting member 26 is seen to expand to the expanded configuration 26'.

Figure 6:
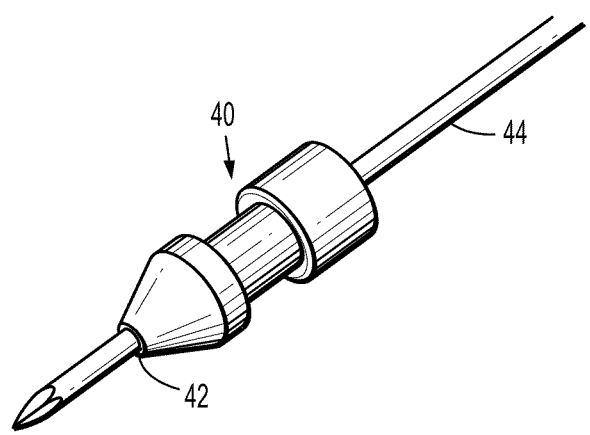
FIG. 6 is a perspective view of an embodiment of an interspinous implant in a compacted state with a guide wire inserted in an internal conduit of the implant.

In embodiments, a compacted interspinous implant 40 includes an internal conduit 42 for receiving a guide wire 44 as shown in FIG. 6. The conduit is coaxial with the longitudinal axis of the implant 40 and dimensioned to receive a guide wire 44. As described more fully below, a guide wire may be used to position a swellable interspinous implant between the spinous processes.

Figure 7:
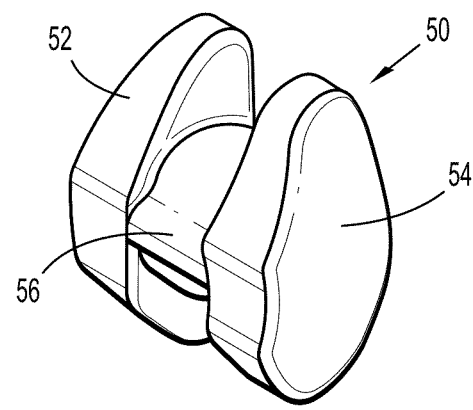
FIG. 7 is a perspective view of an embodiment of an interspinous implant in an expanded state.
Figure 8:
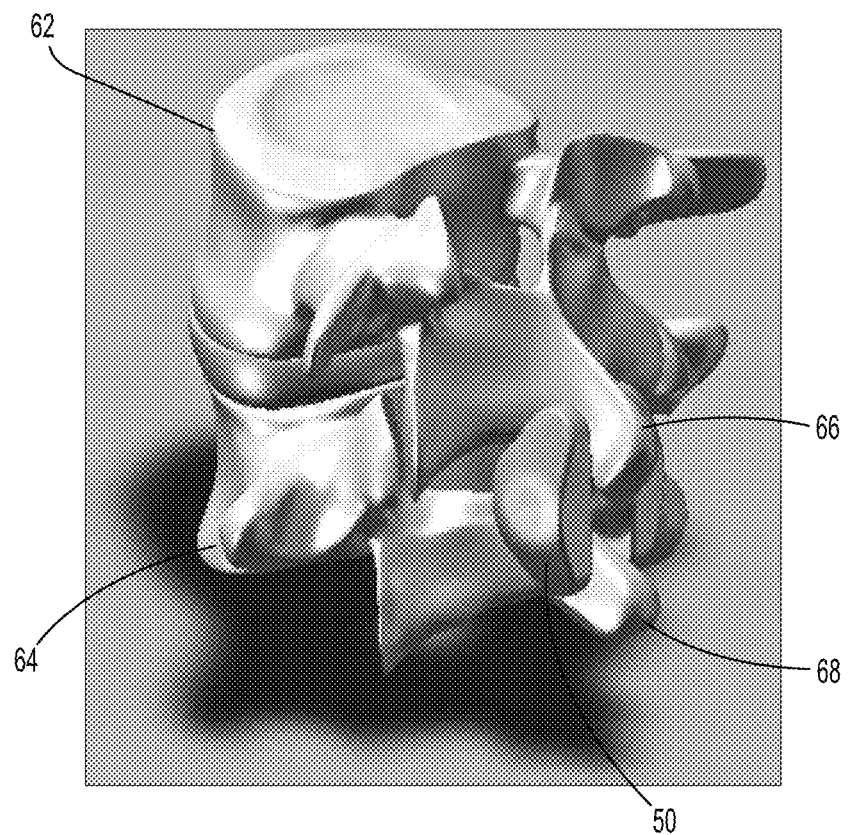
FIG. 8 is a perspective view of the interspinous implant shown in FIG. 7 situated in the interspinous space between two vertebrae.

An additional example of an expanded interspinous implant 50 is shown in FIG. 7. A first retainer end portion 52 is seen to have an oblong ellipsoidal shape. Likewise, the second retainer end portion 54 an oblong ellipsoidal shape corresponding to the shape of first retainer end portion 52. The interconnecting member 56 extends between the two retaining members and is seen to extend from the front of the implant to the back of the implant. FIG. 8 is a perspective view of the implant 50 depicted in FIG. 7 situated between two adjacent vertebrae 62 and 64. The implant 50 is firmly lodged between the superior spinal process 66 and the inferior spinal process 68. The central portion 56 is disposed between the bone architecture defining the interspinous space between the two adjacent vertebrae 62 and 64 and to exert positive pressure against extension via contact with the spinous processes 66 and 68. The oppositely disposed first and second end retainer portions 52, 54 are dimensioned and configured to engage the spinous processes 66 and 68 at their respective outer sagittal faces and anchor the central portion 56 of the interspinous implant in place against the lamina and respective vertebral bodies. The inward facing surfaces of the two respective retainer end portions 52, 54 frictionally engage the outer sagittal faces of the spinous processes 66 and 68.

Figure 9:
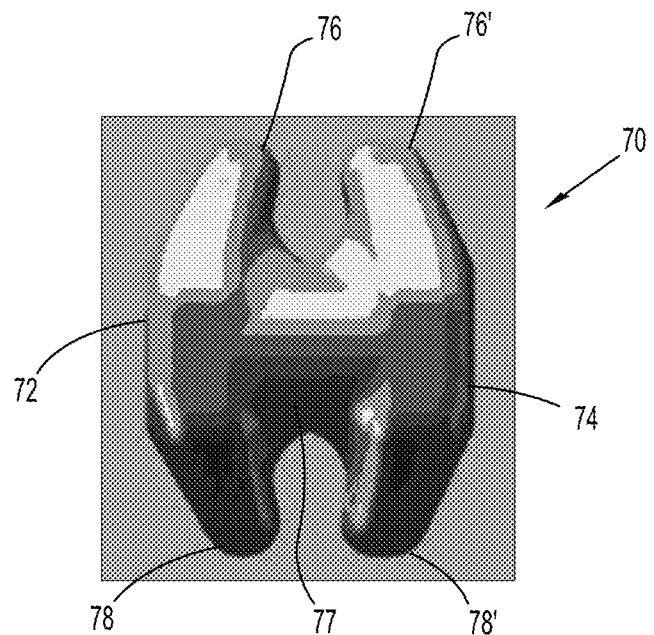
FIG. 9 is a top view of an embodiment of an interspinous implant which has inwardly canted opposing retainer members.
Figure 10:
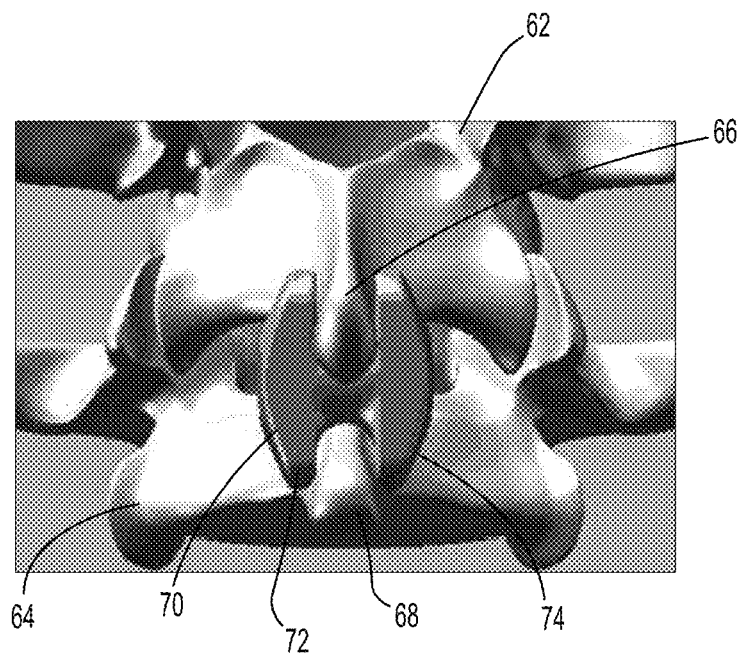
FIG. 10 is a front view of the interspinous implant having inwardly canted opposing retainer members shown in FIG. 9 situated in the interspinous space between two vertebrae.
Figure 11:
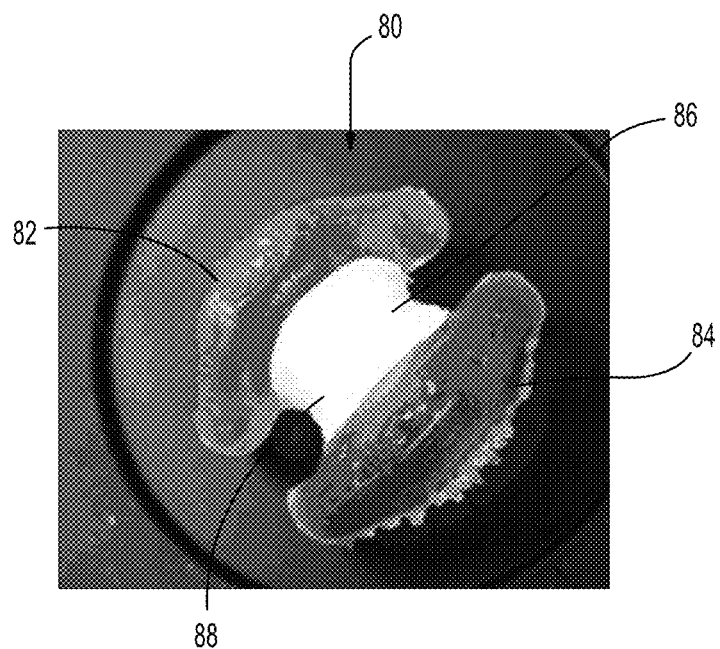
FIG. 11 is a perspective view of an embodiment of an interspinous implant having a wear reducing surface on a centrally disposed cross member connecting two opposing retainer members.
Figure 12:
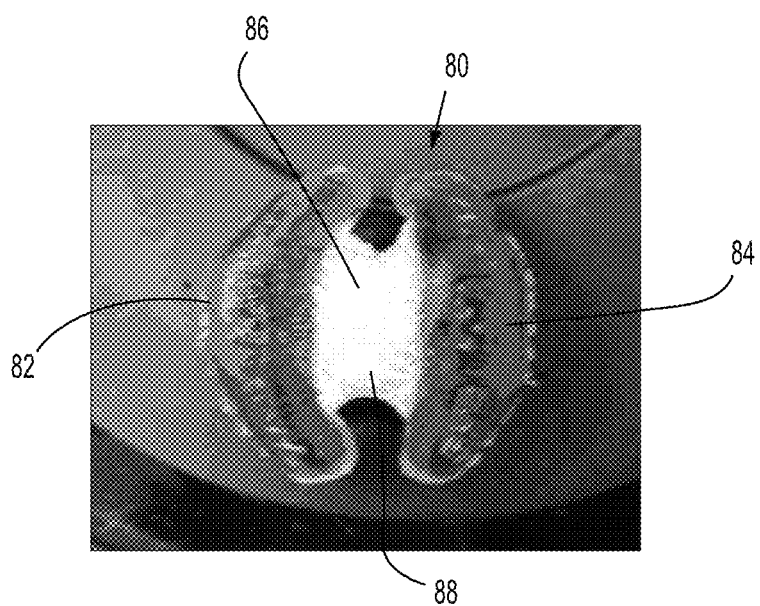
FIG. 12 is a top view of the interspinous implant shown in FIG. 11.

In embodiments, an interspinous implant, e.g., 70 in FIG. 9 includes a first retainer end portion 72 and an opposing second retainer end portion 74 connected by an interconnecting member 77, each oppositely disposed end retainer portion 72, 74 having a top portion 76, 76' and a bottom portion 78, 78' which are each canted toward the corresponding top half and bottom half of the opposing end retainer portions as can be seen in FIG. 9. When the implant is situated in place, as demonstrated in FIG. 10, the inward cant of the retainer portions helps increase the pressure on the outer sagittal faces thus creating a greater degree of frictional engagement between the implant 70 and the outer sagittal faces of the spinous processes 66 and 68. In this manner, a well-defined medial force is created between the opposing first and second end retainer portions 72 and 74 which increases positional stability and resistance to motion. In embodiments, the respective ends of top and bottom portions are canted inwardly towards one another as can be seen in FIGS. 11 and 12.

An interspinous implant herein is swellable and resilient which permits the implant to be inserted to the point of application in its reduced configuration through a minimally invasive incision, e.g., 4-8 mm. Once in place, the implant expands, depending on the method of compaction as discussed herein, either isotopically or anistropically, to its expanded configuration which, due to the swellability and resiliency of the polymer, at least partially conforms to the topography of the interspinous space between adjacent vertebrae. As a result, an interspinous implant according to the present disclosure provides a cushiony custom fit for the implant that, along with the frictional engagement discussed above, avoids the need for rigid, traumatic attachments to the vertebral bone. In addition, the supraspinous ligament is maintained and assists in holding the implant in place. No laminotomy, laminectomy or foraminotomy is necessary.

An advantage of the cushiony nature of the implant allows it to be used in patients with osteoporosis. Typically, such patients have brittle bones which may break under heavy loads. Rigid implants of the prior art would be contraindicated in these patients since they are unyielding and can concentrate too much load on osteoporotic bone, thereby increasing the risk of fracture or breakage. The present implant reduces or eliminates the propensity of weakened, osteoporotic bone to fracture and/or break.

Fluid absorbing polymers are well-suited for manufacturing a swellable, resilient interspinous implant in accordance with the present disclosure. Suitable fluid absorbing polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof. Examples of materials that can be used to form a hydrogel include modified alginates. Alginate is a carbohydrate polymer isolated from seaweed, which can be crosslinked to form a hydrogel by exposure to a divalent cation such as calcium. Alginate is ionically crosslinked in the presence of divalent cations, in water, at room temperature, to form a hydrogel matrix. Modified alginate derivatives may be synthesized which have an improved ability to form hydrogels.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Other polymeric hydrogel precursors include polyethylene oxide-polypropylene glycol block copolymers such as Pluronics™ or Tetronics™, which may be crosslinked by hydrogen bonding and/or by a temperature change. Other materials which may be utilized include proteins such as fibrin, collagen and gelatin. Polymer mixtures also may be utilized. For example, a mixture of polyethylene oxide and polyacrylic acid which gels by hydrogen bonding upon mixing may be utilized. In embodiments, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Water soluble polymers with charged side groups may be crosslinked by reacting the polymer with an aqueous solution containing ions of the opposite charge, either cations if the polymer has acidic side groups or anions if the polymer has basic side groups. Examples of cations for cross-linking of the polymers with acidic side groups to form a hydrogel are monovalent cations such as sodium, divalent cations such as calcium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin. The polymers can be covalently crosslinked as well through the addition of ethylene diamine, NBS or a host of crosslinking agents routinely to react with amino, nitrile, urethane and carboxylic functional groups found on the polymer chain.

Suitable ionically crosslinkable groups include phenols, amines, imines, amides, carboxylic acids, sulfonic acids and phosphate groups. Aliphatic hydroxy groups are not considered to be reactive groups for the chemistry disclosed herein. Negatively charged groups, such as carboxylate, sulfonate and phosphate ions, can be crosslinked with cations such as calcium ions. The crosslinking of alginate with calcium ions is an example of this type of ionic crosslinking. Positively charged groups, such as ammonium ions, can be crosslinked with negatively charged ions such as carboxylate, sulfonate and phosphate ions. Preferably, the negatively charged ions contain more than one carboxylate, sulfonate or phosphate group.

Anions for cross-linking of the polymers to form a hydrogel are monovalent, divalent or trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

In preferred embodiments, the interspinous implant is made of a hydrogel. Prior to coagulation, the liquid form of a suitable hydrogel is used to form the expanded configuration as it would be in the hydrated state. The hydrogel is then coagulated to form the implant in an expanded configuration. The interspinous implant is then dehydrated to a xerogel state which reduces the volume of the implant to the reduced configuration. Many hydrogel polymers behave in a similar manner, which is to say they can be deformed, frozen into a deformed shape and they can maintain that shape indefinitely or until, e.g., a temperature change causes the polymer to "relax" into the shape originally held prior to freezing. This property is often referred to as shape memory or frozen deformation by those skilled in the art.

The temperature at which frozen deformation occurs is referred to as the glass transition temperature or $T_g$. At $T_g$ several polymer properties such as density, entropy and elasticity may sharply change. Many polymers can be mixed with agents that can have a drastic effect on a polymer $T_g$. Polymers which absorb fluid are of particular interest and water is the preferred $T_g$ altering agent. Hydrogels which contain less than about five percent water may be considered dehydrated or xerogels. The $T_g$ of a xerogel will change as it absorbs fluids containing water. Once the $T_g$ becomes lower than ambient the now partially hydrated hydrogel becomes pliant and may be elastically deformed. If the polymer is held in a state of elastic deformation while the $T_g$ is raised above ambient the polymer will maintain the deformed state indefinitely. This can be accomplished by either lowering the ambient temperature (freezing) or by returning the polymer to its xerogel state thus raising the $T_g$.

Using this method, hydrogel articles may be produced with vastly differing xerogel shapes compared to hydrated shapes. This is especially useful in cases such as medical implants where, in delivering a prosthesis into the human body, every care should be taken to reduce trauma to the patient. An implant which is shaped as an hourglass or dumbbell, for instance, is re-shaped into a tapered elongate rod in order to facilitate minimally invasive implantation. Alternatively, a portion of the implant can be compressed as compared to another portion of the implant. Indeed, various frozen shapes may be utilized to facilitate implantation and situation of the implant. See, e,g, FIGS. 1, 3, 6, 18, 19, 21 and 22. Once the implant is indwelling and has absorbed water containing liquids it will substantially return to the expanded shape and maintain that shape indefinitely. As used herein, "substantially" is intended to mean any of "approximately", "nearly" or "precisely."

A swellable, resilient self-retaining interspinous implant in accordance with the present disclosure provides a unique support for the interspinous space by virtue of the ability of the fluid absorbing polymeric medium described herein to swell and deswell based on load. The indwelling implant absorbs fluid and expands in the interspinous space until it becomes constrained by the walls of the space. The hydrophilic nature of the implant causes the implant to imbibe fluid and exert positive pressure against the oppositely disposed spinous processes of the adjacent vertebrae, thus maintaining a certain degree of distraction. During flexion, the implant absorbs fluid and expands, especially in the centrally disposed cross-member, to maintain contact with the superior and inferior faces of the spinous processes as they separate. During extension, the expanded implant exerts mild, yet sufficient force to retard extension when an extension load is applied. Advantageously, the implant does not distort under such loads since fluid is expressed from the implant, thereby allowing the relative volume and mass of the implant to decrease without loss of form. In contrast, an implant made from, e.g., silicone, which does not absorb or express fluids, does not change mass and/or volume under such loads and is forced to distort under loads, e.g., to bulge, buckle and/or elongate. Such distortion can negatively destabilize the implant and the interspinous space. Indeed, if non-fluid absorbing polymeric implant is held in place by oppositely disposed retaining members that exert inward pressure against the outer sagittal sides of adjacent spinous processes, the central portion contained in the interspinous space would deform and elongate under load, thus spreading the retaining members apart and loosening the implant. The risk of implant position failure would be very high under such conditions. This problem is avoided by an implant in accordance with the present disclosure.

A preferred polymer configuration includes two polymer phases of different hydrophilicity, the less hydrophilic phase having higher content of hydrophobic groups and more hydrophilic phase having higher content of hydrophilic groups. The less hydrophilic phase is preferably crystalline and more hydrophilic phase is preferably amorphous, as can be established from X-ray diffraction.

Advantageous hydrophobic groups are pendant nitrile substituents in 1,3 positions on a polymethylene backbone, such as poly(acrylonitrile) or poly(methacrylonitrile). The hydrophilic phase may preferably contain a high concentration of ionic groups. Preferred hydrophilic groups are derivatives of acrylic acid and/or methacrylic acid including salts, acrylamidine, N-substituted acrylamidine, acrylamide and N-substituted acryl amide, as well as various combinations thereof. A particularly preferred combination contains approximately two thirds acrylic acid and its salts (on molar basis), the rest being a combination of plain and N-substituted acrylamides and acrylamidines.

At least one polymeric component is preferably a multiblock copolymer with alternating sequences of hydrophilic and hydrophobic groups. Such sequences are usually capable of separating into two polymer phases and form strong physically crosslinked hydrogels. Such multiblock copolymers can be, for example, products of hydrolysis or aminolysis of polyacrylonitrile or polymethacrylonitrile and copolymers thereof. For convenience, polymers and copolymers having at least about 80 molar % of acrylonitrile and/or methacrylonitrile units in their composition may be referred to as "PAN". Hydrolysis and aminolysis of PAN and products thereof are described, for example, in U.S. Pat. Nos. 4,107,121; 4,331,783; 4,337,327; 4,369,294; 4,370,451; 4,379,874; 4,420,589; 4,943,618, and 5,252,692, each being incorporated herein by reference in their respective entireties.

A preferred fluid absorbing polymer for the interspinous implant is a synthetic composite of a cellular (or domain) type with continuous phase formed by a hydrophobic polymer or a hydrophilic polymer with low to medium water content forming a "closed cell" spongy structure that provides a composite with good strength and shape stability. Examples of suitable polymers are polyurethanes, polyureas, PAN, and highly crystalline multiblock acrylic and methacrylic copolymers. The polymer should be sufficiently permeable to water. More preferably, the continuous phase is formed by a strong hydrophilic polymer with sufficient permeability for water but impermeable to high-molecular solutes. Examples of such polymers are highly crystalline hydrogels based on segmented polyurethanes, polyvinylalcohol or multiblock acrylonitrile copolymers with derivatives of acrylic acid. Typically, suitable polymers for the continuous phase in cellular composites have a water content in fully hydrated state between about 60% by weight and about 90% by weight, preferably between about 65% and about 85% by weight.

The second component of the fluid absorbing polymer may be a highly hydrophilic polymer of high enough molecular weight to prevent permeation of the hydrophilic polymer through the continuous phase. This component is contained inside the matrix of the continuous phase. The entrapped hydrophilic polymers (the so-called "soft block") may be high-molecular weight water-soluble polymers, associative water-soluble polymers or highly swellable hydrogels containing, in a fully hydrated state, an amount of hydration which is preferably at least about 5% greater than the hydrophobic component. For example, the second component hydrated to at least about 65% when the first component is hydrated to about 60%. In other embodiments, e.g., from the second component could be fully hydrated at from about 95% of water and up to about 99.8% of water. Such hydrogels are very weak mechanically. However, it may not matter in composites where such polymers' role is generation of osmotic pressure rather than load-bearing, with e.g., compression strength in full hydration in the range of about 0.01 $MN/m^2$ or lower.

A system with closed cells (or domains) containing highly swellable or water-soluble polymers can form composites with very high swelling pressure as needed for the interspinous implant function. Examples of suitable hydrophilic polymers are high-molecular weight polyacrylamide, polyacrylic acid, polyvinylpyrrolidone, polyethyleneoxide, copolymers of ethyleneoxide and propyleneoxide or hyaluronic acid; covalently crosslinked hydrogels such as hydrophilic esters or amides of polyacrylic or polymethacrylic acids; and physically crosslinked hydrogels, such as hydrolyzates or aminolysates of PAN.

Particularly suitable are associative water-soluble polymers capable of forming very highly viscous solutions or even soft physical gels. Preferred are associative polymers containing negatively charged groups, such as carboxylates, sulpho-groups, phosphate groups or sulfate groups. Particularly preferred are associative polymers formed by hydrolysis and/or aminolysis of PAN to high but finite conversions that leave a certain number of nitrile groups (typically, between about 5 and 50 molar %) unreacted.

Preferred fluid absorbing polymer composites have both a continuous phase and a dispersed phase formed by different products of hydrolysis or aminolysis of PAN. In this case, both components are compatible and their hydrophobic blocks can participate in the same crystalline domains. This improves anchorage of the more hydrophilic component and prevents its extraction or disassociation. The size of more hydrophilic domains may vary widely, from nanometers to millimeters, preferably from tens of nanometers to microns.

The ratio between the continuous discrete phase (i.e., between more hydrophobic and more hydrophilic components may vary from about 1:1 to about 1:100 on a dry weight basis, and a preferred ratio ranges from about 1:2 to about 1:20. Examples of compositions and implants are described in U.S. Pat. Nos. 6,264,695 and 6,726,721, both of which are incorporated herein by reference in their entireties. A preferred method of making the fluid absorbing polymer composite is described in U.S. Pat. No. 6,232,406, herein incorporated by reference in its entirety.

Examples of particularly suitable hydrogel forming copolymers are prepared by a partial alkaline hydrolysis of polyacrylonitrile ("HPAN") in the presence of sodium thiocyanate (NaSCN). The resulting hydrolysis product is a multi-block acrylic copolymer, containing alternating hydrophilic and hydrophobic blocks. Hydrophilic blocks contain acrylic acid, acrylamidine, and acrylamide. In embodiments, for example, a PAN hydrolysate polymer (referred to herein HPAN I) (46±1% conversion of hydrolysis) having the following composition: acrylonitrile units ~53-55%, acrylic acid units ~22-24%, acrylamide units ~17-19%, acrylamidine units ~4-6%, as determined by $^{13}C$ NMR, is dissolved in a suitable solvent such as a 18 55% solution of sodium thiocyanate in water to form a viscous solution. The viscous solution is poured into a porous mold having, e.g., an hourglass shaped cavity. The solution can then be solvent cast, e.g., by solvent exchange (e.g., water for NaSCN). The pores should be sufficiently small as to not permit the polymer to diffuse or leak out of the mold. In another form, the hydrogel used to make the interspinous implant is obtained by reacting an aquagel of PAN, formed by dissolving the polymer in an aqueous solvating solution such as high concentration of sodium thiocyanate. The resulted solution of PAN is thereupon coagulated through addition of a suitable aqueous solvent or water miscible solvent. The coagulum is further reacted in a hydrolyzing basic or acidic medium. The PAN aquagel can then be processed as a thermoplastic and molded to obtain the desired shape. These methods are described in U.S. Pat. No. 4,943,618.

A more rigid fluid absorbing polymer may be another PAN hydrosylate polymer, referred to herein as HPAN II (28±1% conversion of hydrolysis), having the following composition: acrylonitrile units ~71-73%, acrylic acid units ~13-15%, acrylamide units ~10-12%, acrylamidine units ~2-4%, as determined by $^{13}C$ NMR, disolved in ~55% NaSCN which can be solvent cast, washed, dried and cut to a suitable shape.

The interspinous implant optionally includes an interiorly embedded support member. The support member occupies at least a portion of the interior of the implant. The support member is preferably in the form of a fabric or a foil, but may also be a series of individual fibers or ribbons which are arranged in parallel or non-parallel fashion. The fabric may be woven or non-woven and may be in the form of a mesh. The size of interstices in the mesh is not deemed critical and it is contemplated that various mesh sizes are suitable. A fabric support member may be made of a polymeric material which is natural, e.g., cotton, or synthetic, e.g., polyester, polyamide, or other materials such as metal fiber, fiber glass, and carbon fiber. Methods of making fabric from these materials and others are well-known to those skilled in the art. Foils herein may also be made of metal or polymeric material and are well-known. Thus, the support member may be constructed from relatively durable materials including, but not limited to, metal foil, plastic foil, metal fibers, polymeric fibers of materials such as polycarbonate, polyethylene, polypropylene, polystyrene, polyethylene terephthalate, polyamide, polyurethane, polyurea, polysulfone, polyvinyl chloride, acrylic and methacrylic polymers, expanded polytetrafluoroethylene (Goretex®), ethylene tetrafluoroethylene, graphite, etc. Polyester mesh made of Dacron® (commercially available from E. I. du Pont de Nemours and Company) or nylon are especially suitable. These materials can be used either alone, or in a composite form in combination with elastomers or hydrogels. Especially advantageous are mesh, woven, non-woven, perforated, or porous formats of these materials which will allow solid anchoring in the implant. Alternatively, the suppport member may be exteriorly disposed, e.g., a jacket which surrounds all or part of the interspinous implant.

The support member may also be an interiorly disposed braided three-dimensional construct which utilizes unique capabilities manifest by three-dimensional braid architecture. Three-dimensional braiding techniques allow construction of fiber architectures with a high degree of structural integrity and fiber volume fractions, a wide range of pore geometries and pore distribution, and the unique ability to maintain and/or to selectively limit the outer dimensional configuration of the implant while providing a convenient modality for dimensional compression into a desirable implantation configuration. The braided three-dimensional support member is anchored in the implant and provides reinforcement to the implant which increases structural integrity, creep resistance and assists in preventing bulging of the implant under load bearing conditions.

Fibers or strips useful for forming the three dimensional braided support member may be monofilament or multifilament or combinations of the two. Although the term "fiber" generally refers to a flexible, slender, elongated, threadlike object or structure of ellipsoid cross-section, for convenience, "fiber" as used herein also encompasses a "strip", i.e., material which can be elongate and flat. Suitable materials and techniques for forming monofilament of multifilament fibers such as yarn or rovings are well-known to those skilled in the art. For example, suitable fiber forming materials include polyamide, polyethylene terephthalate, polypropylene, polyethylene, PEEK, carbon, ceramic, glass and combinations thereof. Three-dimensional braiding techniques are also well-known to those skilled in the art. See, e.g., Ko, Ceramic Bulletin, Vol. 68, No. 2, pp. 401-414 (1989). Advantageously, the fibers in a braid interlace at angles greater than zero, but less than ninety degrees. The orientation of the fibers or strips in a braid allows for three-dimensional malleability in a three-dimensional fiber architecture. In addition, the void to fiber ratio is adjustable, i.e., the architecture can be made more or less dense depending on the braiding angle and/or geometry of yarn/roving cross-section. The void to fiber ratio can range from about 0.3 to about 3.0.

A particular advantage of three-dimensional braiding techniques is the ability to assume complex structural shapes. By utilizing an advantageous zigzag path within a three-dimensional architecture, the fibers are capable of shortening their length along defined dimensions and to elongate as well, until a desired jamming configuration is achieved. In embodiments, the support member is configured and dimensioned to correspond to the shape of the void in the interspinous cavity. Accordingly, the support member may be configured in the shape of a 2 or 3 dimensional hourglass or dumbbell. In certain embodiments, the support member can have a shape which does not correspond to the exterior shape of the interspinous implant. Concave or convex structures are also contemplated. Alternatively, the three-dimensional support member may be configured into other geometric shapes such as rectangular, conical, frusto-conical or pyramidal. Irregular shapes may also be utilized. The support member may be hollow or filled with braided fiber. In addition, a braided support member may be engineered to be particularly conducive to anisotropic expansion and/or contraction, thus permitting a highly optimized delivery shape. Thus, the braided support member can be made to expand or be stretched along one axis while remaining relatively fixed along another axis. Such anisotropic expansion and contraction may be utilized to enhance preferential swelling of the interspinous implant in predetermined dimensions. In this manner, the support member enhances the ability of the interspinous implant to exert positive pressure against the vertebral processes. Inherent anisotropic contraction may be facilitated by exerting sufficient pressure against the engineered contractile axis, thus allowing the braided support member to be selectively manipulated into a desired implantation shape of reduced and optimized cross-section.

In embodiments, the support member includes a portion that is interiorly disposed and an exteriorly disposed portion which extends out of the body of the implant. The exteriorly disposed portion may be utilized to anchor the implant to surrounding tissue or bone. The exteriorly disposed portion of the support member may be, e.g., oblong, tail shaped and the like, and is adapted and configured to wrap around bone and/or surrounding tissue such as the interspinous ligament.

In embodiments, an interspinous implant optionally includes one or more wear reducing surfaces to prevent contact points between the implant and bone from degrading the implant and/or the bone. The wear reducing surface can be a clearly defined separate layer such as a sheath or patch, or it can be an integral layer which has no clearly defined boundary between the material which makes up the body of the implant and the wear reducing surface. For example, FIG. 11 is a perspective view and FIG. 12 is a top view of an interspinous implant 80 having a first retainer end portion 82 and a second retainer end portion 84 and an interconnecting member 86. The interconnecting central portion of the implant may be subject to a great deal of wear during extension and flexion as it rubs against the opposing vertebral bony surfaces, e.g., the spinous processes. The wear reducing surface serves to protect the interiorly disposed cushiony material which makes up the body of the central portion of the implant and provides a smooth, durable contact surface which reduces friction and consequent wear of the implant and/or bone. FIGS. 11 and 12 show a tubular sheath 88 surrounding the interconnecting member 88 of the implant 80 which acts as a wear reducing surface. Alternatively, a wear reducing patch may be applied to the implant at desired locations where it is determined that frictional engagement is unwarranted. The sheath or patch should be flexible to conform to the changing dimensions of the implant which are contemplated herein. The sheath or patch may be made of a non-porous material which is fashioned from a sheet which, in the case of a tubular structure has two ends which are joined by an adhesive, a hot melt process or any other suitable method known by those skilled in the art. A seamless tubular sheath may be extruded or drawn from suitable materials to form a tube. Suitable materials include olefins such as polyethylene, polyporopylene, and polymers such as PTFE, polyamide, polyethylene terephthalate, silicone and PEEK.

The sheath or patch may also be constructed from woven, non-woven, knit and braided fibers such as those described above in connection with the interiorly embedded support member. A patch or sheath may also be constructed from a porous material which can include membranes made of the above materials or from fibers made of the above materials oriented to provide suitable instital spaces. The sheath or patch may be applied to the implant with or without adhesives. Suitable adhesives are well-known in the art. If applied to the central portion of the implant, a sheath may be held in place by the oppositely disposed end retainer portions without need of an adhesive.

Alternatively, the implant may be constructed such that a layer of durable wear reducing material is integrally formed into the implant. For example, a layer of HPAN II or silicone can be made to surround a softer layer of HPAN I in the central portion of the implant. In the case of HPAN I and II, as described below, the two polymers can be allowed to intermingle and create a smooth transitional boundary between the two polymers.

Figure 5:
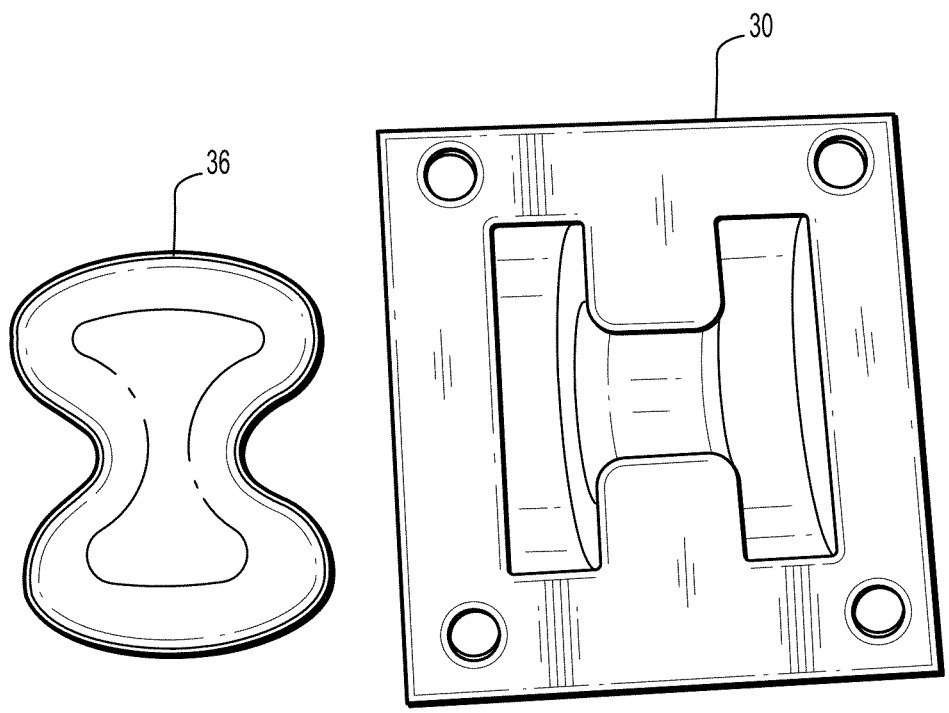
FIG. 5 is a perspective view of an embodiment of an expanded interspinous implant and one-half of a mold for receiving a liquid polymer.

An interspinous implant may be manufactured by providing a mold having, e.g., two corresponding halves such as the one shown in FIG. 5. One half of the mold 30 is shown in FIG. 5. The other half (not shown) is secured to the first half 30 and filled with a liquid swellable polymer such as a fluid absorbing polymer. The polymer is cured or fixed, e.g., by solvent casting, ionic gelation, photo-polymerization and the like. In the case of solvent casting, the mold may be made of material which is impermeable to the fluid absorbing polymer but permeable to water. The mold is placed in a water bath to extract the solvent (e.g., sodium thiocyanate) which causes the polymer to coagulate. The mold may then be opened and any remaining solvent in the interspinous implant is extracted. After curing, the interspinous implant 36 is removed.

In embodiments, an interspinous implant may be manufactured by providing a support member such as a suitably shaped mesh or a three-dimensional braided support member of desired configuration and placing it in a mold. A fluid absorbing liquid polymer is added to the mold and infuses into the interstices of the support member until the support member is preferably saturated. In embodiments, a gap, e.g., about 1 mm, is left between one or more sides of the support member and the walls of the mold. Fluid absorbing liquid polymer is allowed to fill the gap between the mold and the support member. As the support member absorbs fluid absorbing liquid polymer additional amounts of the fluid absorbing liquid polymer can be added. When the fluid absorbing polymer is cured or fixed, e.g., by solvent casting, ionic gelation, photo-polymerization and the like, it solidifies and creates a continuous matrix throughout the support member and also forms a layer surrounding and encapsulating the support member. In the case of solvent casting, the mold may be made of material which is impermeable to the fluid absorbing polymer but permeable to water. The mold is placed in a water bath to extract the solvent (e.g., sodium thiocyanate) which causes the polymer to coagulate. The mold may then be opened and any remaining solvent in the interspinous implant is extracted. If it is desired to leave one or more sides of the interspinous implant open to the support member, then the desired side(s) of the support member is placed up against the wall of the mold to prevent formation of a gap for the liquid fluid absorbing polymer to fill.

In embodiments, the fluid absorbing polymer is made to achieve a strong physical bond to the fibers of the support member by incorporating an initial treatment of the fibers of the member, either before or after the weaving or braiding process, with a relatively hydrophobic fluid absorbing polymer to create an encapsulating layer of the relatively hydrophobic fluid absorbing polymer. For example, a hydrogel such as HPAN II is applied to the fibers as a 10% solution by weight in a solvent (sodium thiocyanate 55% by weight in water) and then coagulated onto the fibers by solvent exchange with an aqueous solution such as water. As the polymer coagulates, it shrinks volumetrically around the fibers, causing a tight physical bond to the fibers. If desired, the treated support member is placed in a mold and a relatively more hydrophilic fluid absorbing polymer in the liquid state is added to create a cohesive continuous polymer matrix which surrounds the support member. For example, a 10% by weight HPAN I in a 55% by weight sodium thiocyanate solution, is added to the mold. The solvent from the HPAN I solution causes the outermost surface of the coagulated HPAN II layer surrounding the braided fibers to dissolve and allow commingling of the HPAN I and HPAN II hydrogel polymers at the surface interface which forms a strong adhesive bond when the HPAN I and commingled hydrogels are coagulated by solvent exchange. It should be understood that the support member is optional and that a mold may be filled without such a support member It is contemplated that regions of more or less modulus of elasticity and durability may be incorporated into the interspinous implant. For example, it may be desirable to place a relatively more rigid fluid absorbing polymer at the top and bottom of the interspinous implant, e.g., the portions which contact the vertebral bone. As discussed above, a wear reducing surface may be advantageous, e.g., such as in the central portion of the implant. Accordingly, a liquid fluid absorbing polymer such as HPAN II can initially be added to the mold to create a first layer, followed by placement of the optional support member into the liquid polymer such that the polymer covers and is absorbed into the bottom, e.g., one-third of the reinforcement member. Increasing air pressure can speed the process of saturation of the implant. After a sufficient amount of liquid polymer is absorbed, it can be cured or fixed. If a softer layer of fluid absorbing polymer is desired in the center section of the interspinous implant, a hydrogel such as HPAN I can be added over the bottom layer to fill the mold to, e.g., ⅔ capacity. After the HPAN I is absorbed sufficiently into the reinforcement member, it can be cured or fixed to create a relatively soft middle layer. A third, more rigid layer can then be created by filling the rest of the mold with, e.g., HPAN II and curing or fixing it by solvent casting. It should be understood that any number of layers of varying or the same thickness may created in this fashion. In addition, different fluid absorbing polymers can be used to create zones with different properties. If desired, an adhesive can be added between adjacent layers to insure bonding or, e.g., in the case of the HPAN polymers, the layers can be made to naturally adhere to one another. In embodiments, one or more layers of liquid fluid absorbing polymer can be placed on top of other liquid layers of fluid absorbing polymer and then cured. Differences in density keep the layers from completely intermixing. Some co-mingling of liquid fluid absorbing polymers at layer interfaces can provide for an advantageous smooth transition between layers and reduce or eliminate the need for an adhesive between layers.

In embodiments, one or more tethers such as a string, suture, etc., are incorporated into the interspinous implant. The tether may be utilized in positioning or maintaining the position of the interspinous implant, or its components, during manufacture in molds, and after manufacture as a device for positioning the interspinous implant within an interspinous space. The tether may be simply placed in a central location within the hollow cavity of a support member prior to filling with a liquid fluid absorbing polymer and is then present when the cavity is filled. Alternatively, a tether may be incorporated into the center of a mold when a liquid fluid absorbing polymer insert is coagulated. Alternatively, the tether may be attached directly to the support member at either an interior location or an exterior location if the support member extends out of the fluid absorbing body of the implant.

In embodiments, the interspinous implant includes an internal conduit which is made by placing a tube of predetermined diameter in the mold and then filling the mold with liquid polymer. After coagulation, the tube is removed from the implant leaving a hollow conduit. In embodiments, the conduit is coaxial with the longitudinal axis of the implant and dimensioned to receive a guide wire. See FIG. 6. In embodiments, the tube is pushed through the center of a three dimensional-braid support member and the combination is placed in the mold. Liquid polymer is then added to the mold and allowed to infuse into the interstices of the support member. The mold is the filled with the liquid polymer which is then coagulated. The tube is then removed to leave a conduit for receiving a guide wire.

Upon completion of the solvent exchange extraction process the interspinous implants may be hydrated to their fullest extent (~90% equilibrium water content (EWC)). In this fully hydrated state the interspinous implant is readily deformed under modest loads and the hydrogel, e.g., HPAN I OR HPAN II, glass transition temperature ($T_g$) is well below room temperature. This is the "relaxed" state of the interspinous implant, the state to which it will return after loading below the critical level. The critical level is the point at which permanent deformation occurs and is further discussed below. In order to provide a reduced configuration (also referred to herein as the first configuration), the interspinous implant may be allowed to dehydrate and enter the xerogel state. A considerable amount of the implant's volume is lost when in the xerogel state as compared to the hydrated state. Advantageously, the fully hydrated interspinous implant may be deformed into a desirable insertion shape and the temperature of the interspinous implant is lowered below its $T_g$ (near freezing point of water). Such an interspinous implant is in a state of "frozen deformation" and it would retain that deformed shape indefinitely. Once the interspinous implant is warmed above its $T_g$, however, the interspinous implant would recover to its original memorized configuration.

The $T_g$ of the hydrogel increases with decreasing water content. This characteristic is exploited by simultaneously raising the $T_g$ while deforming the interspinous implant into a desired shape. In other words, as the interspinous implant dehydrates it is freezing the position of the polymer chains. To regain the original shape of the interspinous implant, the $T_g$ may be lowered by hydration.

In order to obtain a preferred rod-shape having an optimal cross-sectional ellipsoid shape for implantation, e.g., suppository, bullet, tapered cylinder, arrow, etc., from, e.g., a dumbbell-shaped or hourglass-shaped interspinous implant, reduction in volume deformation is advantageously maintained radially, substantially parallel with the longitudinal axis. This is accomplished by placing the implant within a radially collapsible member for exerting circumferential compression on an object, e.g., an interspinous implant, contained within the member. Suitable radially collapsible members include, e.g., a flexible sleeve such as a braided sock or tube, a flexible coil, iris diaphragm, collapsible loop, etc. In a preferred embodiment, the radially collapsible member is porous or semipermeable so that water, either as liquid or as vapor, passes through the member. The collapsible member may be made of an elastic material such as rubber or neoprene fabric which has been made porous by any technique known to those skilled in the art, or a woven or non-woven mesh or braid. The collapsible member may also be made of a flexible metal having sufficient porosity to allow water to exit from the implant. The collapsible member does, however, need to be stiff enough to be able to exert sufficient compressive force when tension is applied to compress the interspinous implant, i.e., it should not be so elastic that it deforms without being able to exert sufficient compressive force.

In operation, the radially collapsible member exerts substantially equilateral circumferential compression on the interspinous implant by substantially uniformly decreasing in diameter while contacting the implant. The preferred porous nature of the collapsible member allows water from the implant to escape into the surrounding environment so that the interspinous implant can become dehydrated. In embodiments, the sleeve radially collapsible member is stretched in length which causes the inner diameter to decrease, thus compressing the interspinous implant, including, e.g., a braided three-dimensional reinforcement member, into a desired implantation configuration. A more complete description of a suitable radial compression process is described in U.S. application Ser. No. 11/303,767, herein incorporated by reference in its entirety. Other methods of reducing the profile of the interspinous implant include folding or rolling the interspinous implant into, e.g., bellows, a taco shape or a cigar shape.

The collapsible member is loaded in tension via any tensioning device known to one skilled in the art, e.g., a pneumatic cylinder, a hydraulic cylinder, springs, weights, pulleys, etc. The tension on the collapsible member can be precisely controlled by regulating the pressure within the tensioning device, translating into constant, controlled radial load on the interspinous implant. In the case of a sleeve collapsible member, once the interspinous implant is loaded into the collapsible member and the collapsible member is tensioned, three things occur: the interspinous implant dehydrates, the interspinous implant deforms, the collapsible member extends. By varying the tension on the collapsible member, the length of the interspinous implant can be extended, thereby decreasing the minor axis and height. This can also be controlled, to some extent, by the speed of dehydration (temperature, pressure and humidity), with longer dehydration time producing longer interspinous implant length and vise versa. In certain embodiments, one portion of the collapsible member is made to collapse further than other portions to define an implant having one end which is relatively more compressed than the other end. For example, see FIGS. 1 and 3.

There are two concerns with respect to drying time and collapsible member tension that should be considered. The first is creep, which may set in if the dehydration time is extended unreasonably long (over several days). The second is permanent deformation which may occur if excessive stress is applied to the implant. Both of these concerns only occur at critical point extremes which are to be avoided. Permanent deformation may occur in the hydrogel implant if the soft-block domains of the polymer are displaced to a point where they cannot reorient themselves into the original lattice configuration, i.e., the memorized shape. This can happen, e.g., by either deforming the original shape so severely that many of the bonds which hold the soft-blocks in place are severed, or by heating the implant sufficiently above the $T_g$ to cause the soft-block domains to permanently or irrevocably assume a new configuration outside of the originally contemplated structure, which causes an undesirable change in shape. Thus, the melting point of the soft block should not be exceeded. The melting point of the soft block may vary based on the amount of water content. Such melting points may be determined by conventional techniques known to those skilled in the art. For example, at 18% hydration of HPAN I, permanent deformation is manifest at temperatures over 105° C.

In general and in a preferred embodiment, the majority of the dehydration process should occur at room temperature over an extended period of time (e.g., 18 to 36 hours). The interspinous implant can be monitored to determine the extent of dehydration and the time period adjusted accordingly. Relative humidity, air circulation, air pressure and room temperature should be controlled during this period. Especially preferred conditions are about 21° C. at 50% relative humidity under moderate airflow. Once the interspinous implant has reached <~30% water content it may be forced dry at elevated temperature, e.g., from about 25° C. to about 105° C. for typically less than about 24 hours to rapidly remove remaining water. As above, the state of dehydration may be monitored to determine if greater or lesser amounts of time are needed. When the interspinous implant is substantially completely dehydrated, the implant is fairly rigid in its state of frozen deformation. Alternatively, a slight degree of hydration provides some flexibility to the implant. The less dehydrated, the more flexible. It is contemplated herein that "substantially dehydrated" preferably encompasses from about 12% or less, to about 30% water by weight of the implant.

Upon completion of forced dehydration, the interspinous implant is extremely stable in terms of shelf life, providing that it is kept dry. Even brief exposure to humidity during the sterilization process should not have significant effects. Temperatures above about 80° C. should be avoided for extended periods as this may bring the implant above its $T_g$ if it has absorbed some small amount of water vapor.

Surface irregularities may be present on a dehydrated compressed implant which was compressed as described above by a radially collapsible member by virtue, e.g., of some extrusion of the hydrogel through pores or through interstitial spaces of the member. For example, a woven or non-woven collapsible sleeve may have interstitial spaces that allow hydrogel to extrude therein under compressive force. In addition, after radial compression, as described above, the dimensions of the implant may be different than the ultimate dimensions desired by the practitioner. Both of these instances can be remedied by post-compression thermoforming of the interspinous implant. In this aspect, a dehydrated, compressed interspinous implant is placed within a mold which may be advantageously pre-heated to about 70-150° C., but more preferably, closer to the melting point of the polymer, e.g., about 105° C. Care must be taken to avoid subjecting the interspinous implant to excess heat which causes the hydrogel to exceed its critical point, and thus causing permanent deformation of the interspinous implant. If the temperature is high, the interspinous implant must be quickly removed from the mold to avoid permanent deformation. The mold is machined to the exact desired final dimensions of the xerogel interspinous implant and essentially irons out surface roughness to a substantially smooth surface, which is less abrasive to surrounding tissue when implanted. If desired, and if the xerogel implant is compressed by a radially compressive member or by gas compression, but has not achieved, e.g., an ideal enough straight rod-like configuration, or if the ends are not sufficiently blunted or otherwise tapered, post-compression thermoforming may be utilized to fine tune the shape as well as remove any surface irregularities which may be present. Post-compression thermoforming may also be utilized to bend an interspinous implant to a desired configuration, e.g., to a boomerang shape.

An interspinous implant according to the disclosure herein may contain a medicinal agent. "Medicinal agent" is used in its broadest sense and it includes any substance or mixture of substances which may have any clinical use. It is to be understood that medicinal agent encompasses any drug, including hormones, antibodies, therapeutic peptides, etc., or a diagnostic agent such as a releasable dye which has no biological activity per se. Thus, in its broadest aspect, a method of delivery herein may be defined as the release of any substance for clinical use, which may or may not exhibit biological activity.

Examples of medicinal agents that can be used include anticancer agents, analgesics, anesthetics, anti-inflammatory agents, growth factors such as BMPs, antimicrobials, and radiopaque materials. Such medicinal agents are well-known to those skilled in the art. The medicinal agents may be in the form of dry substance in aqueous solution, in alcoholic solution or particles, microcrystals, microspheres or liposomes. An extensive recitation of various medicinal agents is disclosed in Goodman and Gilman, The Pharmacological Basis of Therapeutics, 10th ed. 2001, or Remington, The Science and Practice of Pharmacy, 21 ed. (2005). As used herein, the term "antimicrobial" is meant to encompass any pharmaceutically acceptable agent which is substantially toxic to a pathogen. Accordingly, "antimicrobial" includes antiseptics, antibacterials, antibiotics, antivirals, antifungals and the like. Radiopaque materials include releasable and non-releasable agents which render the interspinous implant visible in any known imaging technique such as X-ray radiographs, magnetic resonance imaging, computer assisted tomography and the like. The radiopaque material may be any conventional radiopaque material known in the art for allowing radiographic visualization of an implant, and may be, e.g., metal wire or flakes made from a biocompatible material, such as titanium, tantalum, stainless steel, or nitinol; or metallic salts (such as barium compounds).

Medicinal agents may be incorporated into the interspinous implant at various points in the manufacturing process. For example, a suitable medicinal agent can be mixed with a fluid absorbing liquid polymer before it is cured or fixed. Alternatively, a suitable medicinal agent may be dissolved into a solvent cast solution and then diffused into the hydrogel in accordance with normal kinetic principles. If the interspinous implant is then dehydrated, the medicinal agent collects in the interstices of the hydrogel and/or the braided three-dimensional reinforcement member.

A dehydrated interspinous implant according to the disclosure herein may be sterilized by any suitable conventional means, e.g., ethylene oxide, irradiation, etc. and packaged for distribution. A kit containing the sterilized interspinous implant and a package insert describing the interspinous implant, along with instructions is useful for medical practitioners.

Techniques for implanting surgical devices in the interspinous space are well-known. In the present case, minimally invasive implantation techniques are improved and facilitated by the reduced dimension and overall configuration of the first configuration. In addition, the ability to provide custom implantation shapes allows an optimal insertion shape to be manufactured. Utilization of a guide wire delivery system allows percutaneous delivery of the implant and an even smaller incision to be made than is normally used, e.g., in the case of cannulas. For example, a small incision is made proximate to the interspinous space that will receive the implant. The interspinous ligament is then dilated using, e.g., a bent awl. A distractor is used to separate the spinous processes and open the interspinous space for receiving the implant. The implant is then guided into the interspinous space with the guide wire. As seen in FIG. 6, a proximate end of the implant resembles the head of an arrow and leads the implant into the interspinous space. The implant is pushed across the interspinous space until the inwardly facing portion of the distal end portion of the implant contacts an outwardly facing sagittal portion of the spinous process. The proximate end pushes through and acts like a barb to engage the other side of the spinous process. The guide wire is then removed from the implant. As the implant expands to the shape, e.g., shown in FIG. 7, internal conduit is optionally compressed and collapses upon itself and the opposing ends of the implant envelope the opposing sides of the spinous processes of the vertebrae to anchor the implant in place as shown in FIG. 8. In addition, the interspinous space is occupied by the central portion of the implant as described above. In operation, the implant gently distracts the interspinous space by virtue of its ability to swell and be resilient. The polymeric materials and optional support members described herein provide a soft, yet resilient, shock absorbing cushion to maintain a distracted interspinous space. In this manner, reinforcement is provided to damaged and/or healing discal architecture and nerve compression on extension is prevented and alleviated.

The following example is included to illustrate certain features in connection with a swellable interspinous stabilization implant herein. Since it is merely exemplary, the example is not intended to limit any aspect of the disclosure of this specification.

EXAMPLE

Surgical Insertion of a Swellable Interspinous Implant

Figure 13:
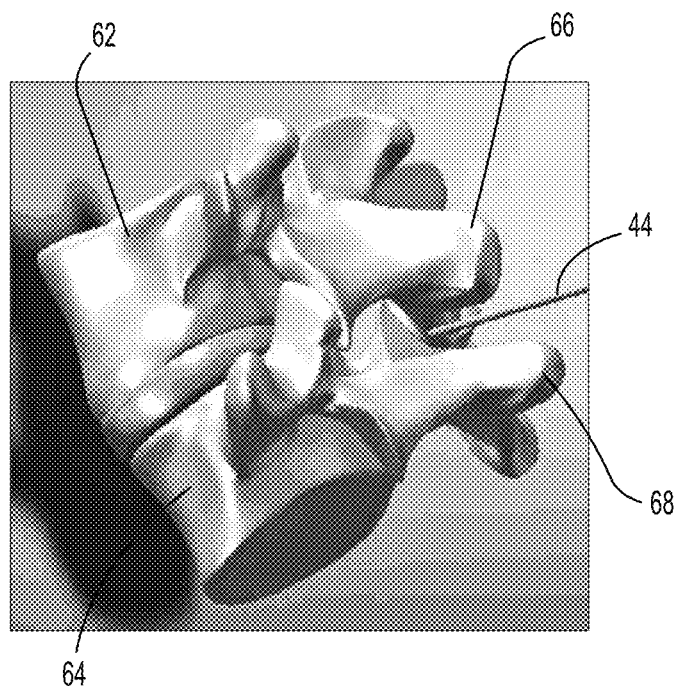
FIG. 13 is a perspective view of two adjacent vertebrae receiving an embodiment of a guide wire pursuant to a posterior implantation approach.
Figure 14:
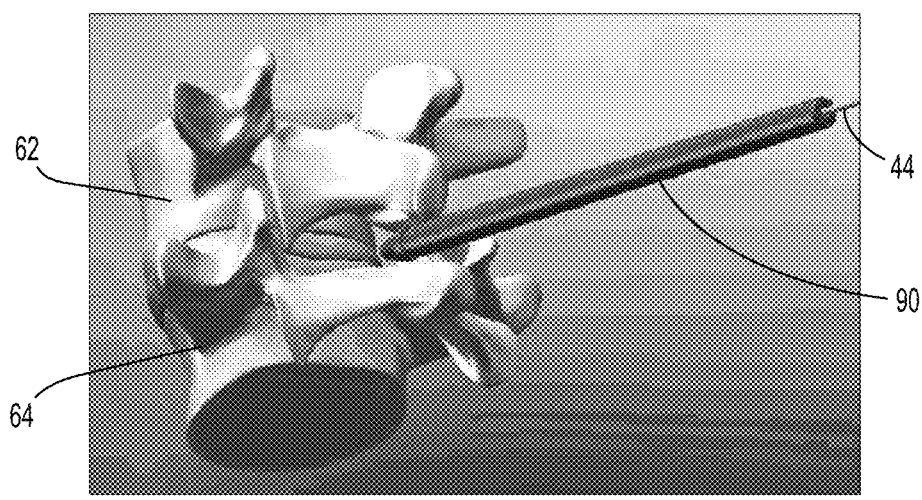
FIG. 14 is a perspective view of an embodiment of a dilator inserted between two adjacent vertebrae using the guide wire as a coaxial guide pursuant to a posterior implantation approach.
Figure 15:
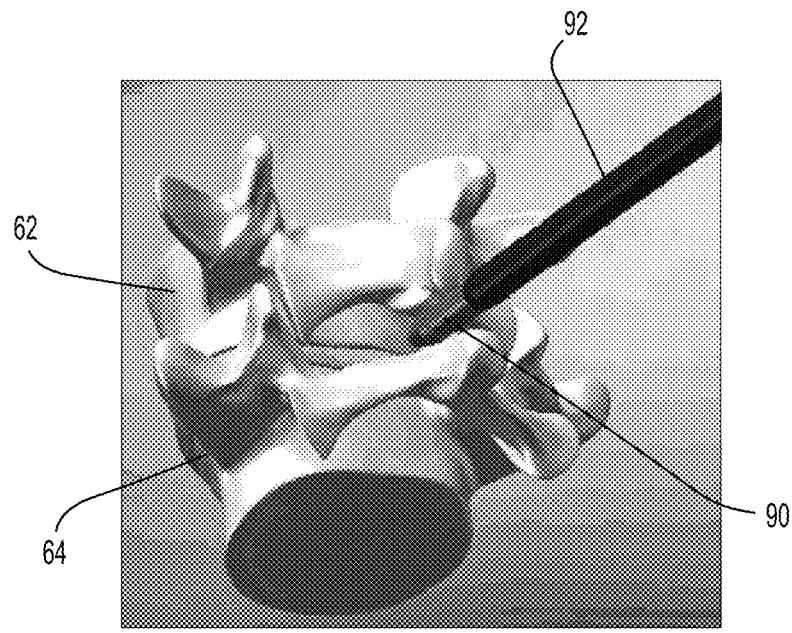
FIG. 15 is a perspective view of an embodiment of a second, larger dilator coaxially inserted over a dilator as shown in FIG. 14 and inserted between two adjacent vertebrae pursuant to a posterior implantation approach.
Figure 16:
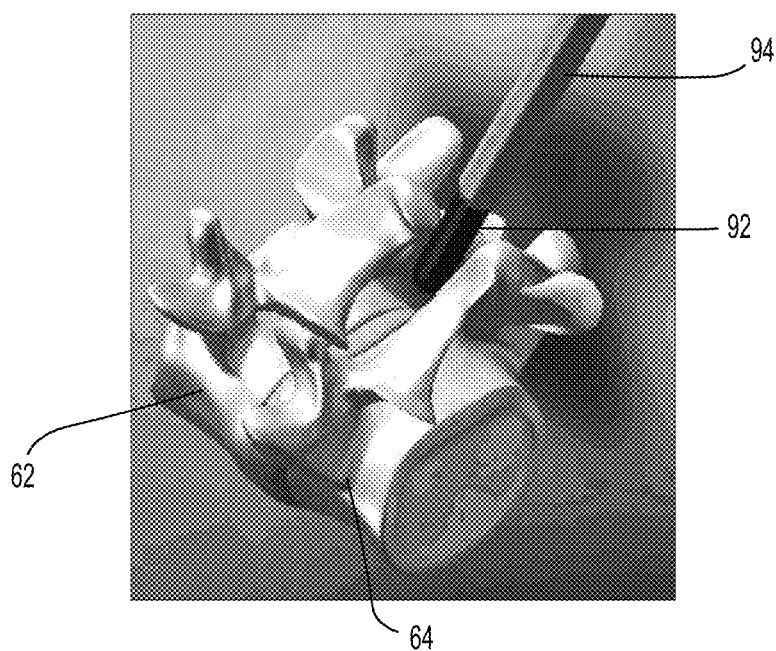
FIG. 16 is a perspective view of an embodiment of an insertion cannula coaxially inserted over a dilator as shown in FIG. 15 prior to insertion between two adjacent vertebrae pursuant to a posterior implantation approach.
Figure 17:
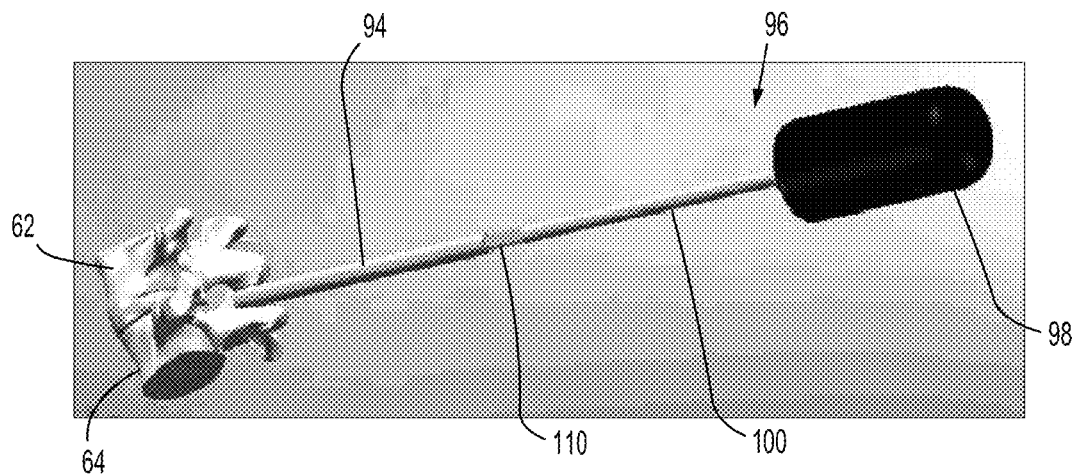
FIG. 17 is a perspective view of an embodiment of an implant insertion device positioned to push a dehydrated swellable interspinous stabilization implant between two adjacent vertebrae pursuant to a posterior implantation approach.
Figure 18:
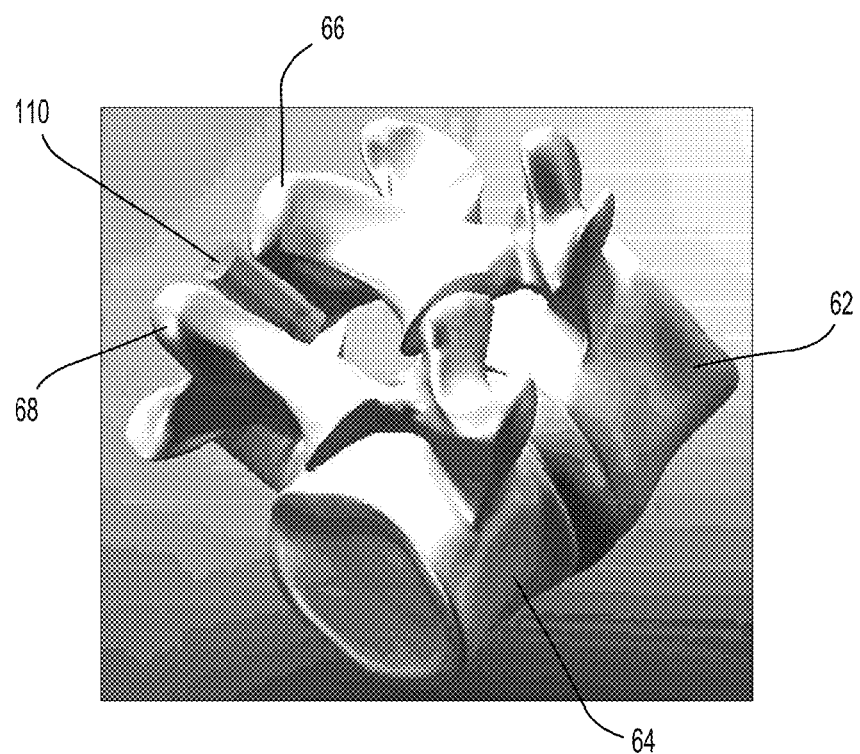
FIG. 18 is a perspective view of an embodiment of a dehydrated, compacted rod shaped swellable interspinous stabilization implant situated in the interspinous space between two vertebrae pursuant to a posterior implantation approach.
Figure 19:
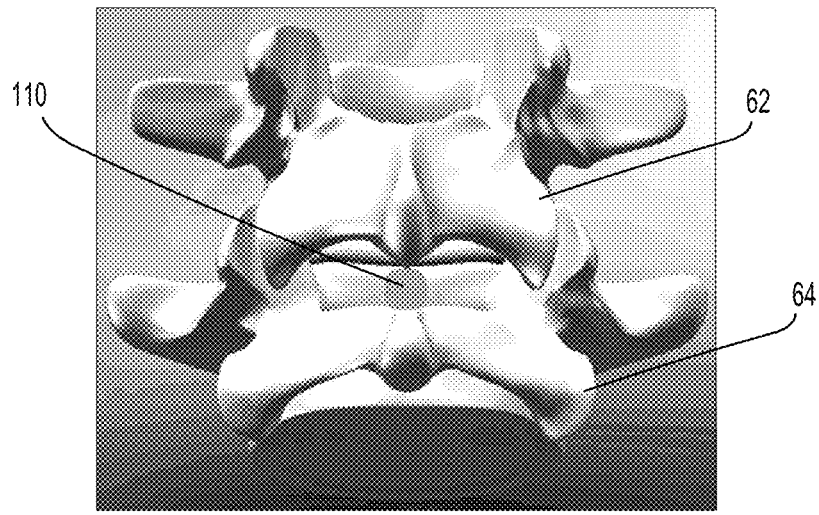
FIG. 19 is a posterior view of an embodiment of a dehydrated, compacted rod shaped swellable interspinous stabilization implant situated in the interspinous space between two vertebrae pursuant to a posterior implantation approach.
Figure 20:
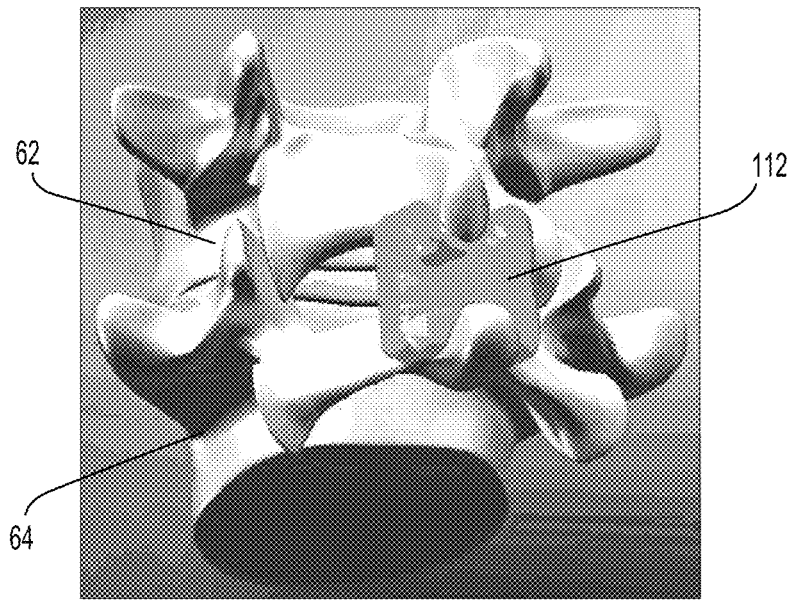
FIG. 20 is a perspective view of the hydrated, expanded swellable interspinous stabilization implant as shown in FIG. 19 situated in the interspinous space between two vertebrae pursuant to a posterior implantation approach.
Figure 21:
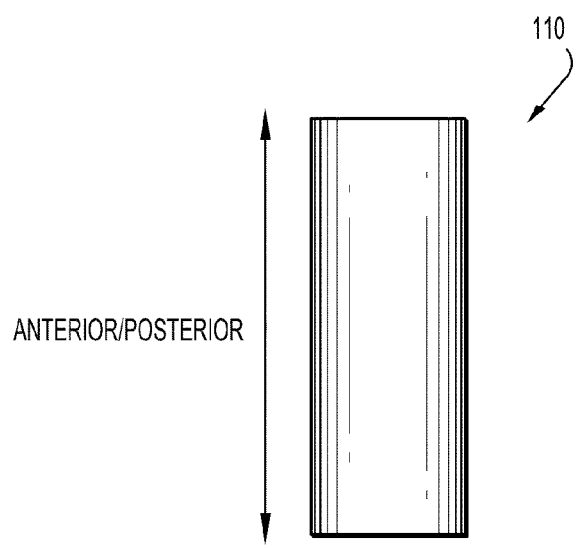
FIG. 21 is a top view of a dehydrated, compacted swellable interspinous stabilization implant as shown in FIG. 19 showing an anterior/posterior orientation.
Figure 22:
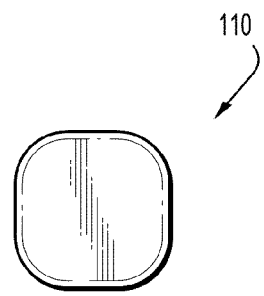
FIG. 22 is a front view of the dehydrated compacted swellable interspinous stabilization implant shown in FIG. 21.
Figure 23:
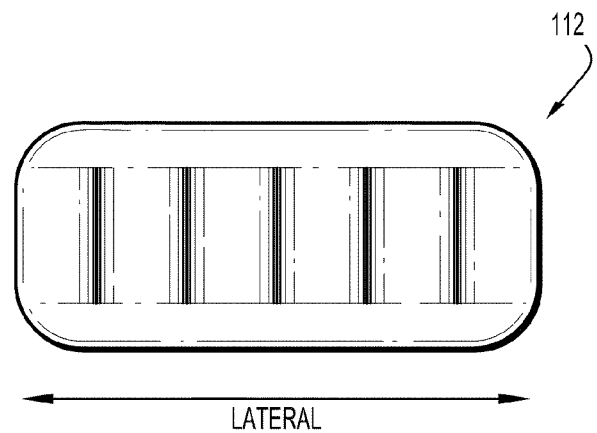
FIG. 23 is a top view of the swellable interspinous stabilization implant shown in FIG. 21 in an expanded configuration and depicting a lateral axis.
Figure 24:
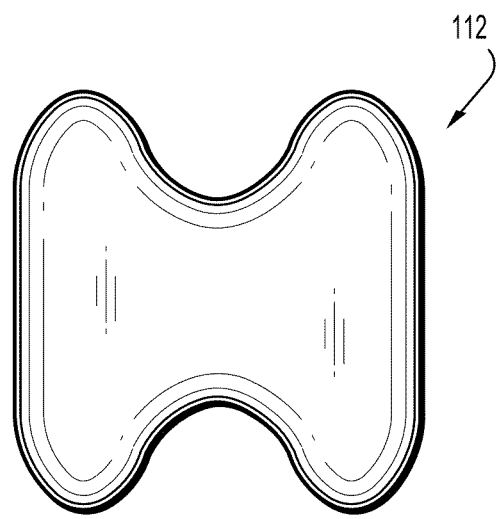
FIG. 24 is a front view of the swellable interspinous stabilization implant shown in FIG. 21 in an expanded configuration

A patient is placed into the prone position on a Wilson frame. Fluoroscopic imaging is then used to verify levels of dissection and appropriate visualization of the spinous processes and vertebral bodies. Skin markings using a skin marker are made. The patient's spine is then sterilely prepped and draped. Using a direct posterior approach a small lumbar midline incision is made. A 1.6 mm k-wire 44 is inserted into the opening. Using fluoroscopic imaging, depth and placement are verified. See FIG. 13. Once correct placement and depth of the guide wire 44 (k-wire) is verified an initial dilator 90 is inserted over the k-wire 44. See FIG. 14. Following successful placement of the initial dilator 90 a second dilator 92 is inserted coaxially over the initial dilator 90 to further distract the interspinous space between the vertebrae 62 and 64. See FIG. 15. If indicated, consecutively larger dilation cannulas are inserted over the initial dilator 90 and second dilator 92 until desired sized dilator is reached. Once the desired distraction has been reached, an insertion cannula 94 is slid over the dilators. See FIG. 16. Following successful placement of the insertion cannula 94, the k-wire 44 and all insertion dilators, e.g., 90, 92 are removed. Insertion cannula 94 placement is verified using fluoroscopic imaging. A rod-shaped dehydrated implant 110 of predetermined size is inserted into the insertion cannula and is pushed into place using the implant insertion device 96 as shown, e.g., in FIG. 17. The implant insertion device 96 includes a handle 98 and an extension rod 100 having an end which removably holds the implant 110. The insertion cannula 94 and implant insertion device 96 are removed, leaving the dehydrated implant 110 in the interspinous space. Fluoroscopic imaging is used to verify position of the implant 110. See FIGS. 18 and 19. The implant 110 and surrounding tissue are irrigated using normal saline solution and periodically thereafter for ten minutes to allow the implant 110 to begin swelling. The patient is closed using established closing procedures. As depicted in FIG. 20, the dehydrated implant 110 swells and fills the interspinous space, reaching its hydrated, working volume, 112. FIGS. 21 and 22 illustrate a rod shaped compacted implant 110. The anterior/posterior aspect is represented by the arrow in FIG. 21. FIG. 23 illustrates a front view of the rod shaped implant 110. FIGS. 23 and 24 illustrate the expanded implant 112 after the dehydrated implant 110 has absorbed fluid. FIG. 23 is a top view of the implant 112 with the lateral aspect illustrated by the arrow. FIG. 24 is a front view of the expanded implant 112.

It should be understood that the examples and embodiments of the invention provided herein are preferred embodiments. Various modifications may be made to these examples and embodiments without departing from the scope of the invention which is defined by the appended claims. For example, those skilled in the art may envision additional polymers and/or hydrogels which can be compacted and shaped according to the techniques described herein. Similarly, the shapes of the compacted and hydrated or expanded interspinous implant described herein are exemplary and any suitable compacted and/or expanded interspinous implant shape can be subjected to the techniques described herein to create an optimally shaped, substantially dehydrated interspinous implant for minimally invasive insertion into the disc space. Those skilled in the art can envision additional radially collapsible members for exerting substantially uniform radial compression on the implant which are not set forth herein. In addition, process parameters such as temperature, humidity, pressure, time and concentration may be varied according to conventional techniques by those skilled in the art to optimize results.

What is claimed is:

1. A swellable, resilient self-retaining interspinous implant which comprises a fluid absorbing polymer which expands from a substantially dehydrated compact first configuration having from about 12% to about 30% water by weight of the implant to an expanded second configuration upon absorption of fluid and which is dimensioned and configured to fit between two spinous processes of adjacent vertebrae, such that when the implant is in the first configuration the implant includes a first retainer end portion having a three dimensional cone shape and an oppositely disposed second retainer end portion which are connected by a centrally disposed transverse cross member, the cross member having a smaller cross-section than the end portions, and when the implant is in the second expanded configuration the first retainer end portion is expanded, the oppositely disposed second retainer end portion is expanded and the centrally disposed transverse cross member is expanded, the first and second retainer end portions being dimensioned and configured to frictionally engage the spinous processes at their respective outer sagittal faces when in the first and second configurations.

2. A swellable, resilient self-retaining interspinous implant according to claim 1, wherein when in the second configuration a space is defined between the first retainer end portion and the second retainer end portion and the first retainer end portion has an upper end and a lower end, the second retainer end portion has an upper end and a lower end, wherein the respective upper ends and lower ends of the first and second retainer end portions are canted inwardly towards one another to define a distance between the respective ends of the first and second retainer end portions that is less than the distance between the first and second retainer end portions at a central portion between the respective ends of the first and second retainer end portions and the cross member.

3. A swellable, resilient self-retaining interspinous implant according to claim 1, wherein the cross member is dimensioned and configured such that when in the second configuration, the cross member has a volume that is greater than the space between two adjacent superior and inferior spinous processes such that when the spinous processes are in a neutral position the cross member is compressed slightly.

4. A swellable, resilient self-retaining interspinous implant according to claim 1, wherein the compact first configuration includes a portion that is rod-shaped.

5. A swellable, resilient self-retaining interspinous implant according to claim 1, further comprising an interiorly disposed support member occupying at least a portion of the interior of the implant.

6. A swellable, resilient self-retaining interspinous implant according to claim 5, wherein the support member extends out of the fluid absorbing polymer.

7. A swellable, resilient self-retaining interspinous implant according to claim 6, wherein the support member includes an exteriorly disposed portion extending out of the fluid absorbing polymer that is dimensioned and configured to be attached to surrounding tissue and/or bone.

8. A swellable, resilient self-retaining interspinous implant according to claim 5, wherein the support member is selected from the group consisting of fabric, foil and three-dimensional braid.

9. A swellable, resilient self-retaining interspinous implant according to claim 5, further comprising a tether attached to the support member for securing the implant to bone or tissue.

10. A swellable, resilient self-retaining interspinous implant according to claim 1, wherein the fluid absorbing polymer expands from the first configuration to the second configuration due to a shape memory property of the polymer.

11. A swellable, resilient self-retaining interspinous implant according to claim 1, wherein the polymer swells upon absorption of fluid and compresses by expression of fluid based upon load applied by the two spinous processes of adjacent vertebrae.

12. A swellable, resilient self-retaining interspinous implant according to claim 1, further comprising an internal conduit.

13. A swellable, resilient self-retaining interspinous implant according to claim 12, wherein the internal conduit is adapted and configured to receive a guide wire along its length.

14. A swellable, resilient self-retaining interspinous implant according to claim 1, further comprising a tether attached to the implant for securing the implant to bone or tissue.

15. A swellable, resilient self-retaining interspinous implant according to claim 1, wherein the implant further comprises a plurality of layers of fluid absorbing polymer, one or more of the layers having a different modulus of elasticity as compared to another layer.

16. A swellable, resilient self-retaining interspinous implant according to claim 1, wherein the fluid absorbing polymer is a hydrogel.

17. A swellable, resilient self-retaining interspinous implant according to claim 16, wherein the hydrogel is a polyacrylonitrile.

18. A swellable, resilient self-retaining interspinous implant according to claim 1, further comprising a medicinal agent.

19. A swellable, resilient self-retaining interspinous implant according to claim 1, further comprising a wear reducing surface.

20. A swellable, resilient self-retaining interspinous implant according to claim 19, wherein the wear reducing surface is a durable sheath dimensioned and configured to fit over the cross member.

21. A swellable, resilient self-retaining interspinous implant according to claim 19, wherein the wear reducing surface is a durable patch dimensioned, configured and positioned on the implant to contact bone thereby reducing wear of the implant caused by contact between the implant and bone.

22. A swellable, resilient self-retaining interspinous implant according to claim 1, wherein the three dimensional cone shape includes a pointed apex.

23. A method of treating a degenerative condition of the spine comprising creating an incision and inserting, through the incision, between two spinous processes of two adjacent vertebrae, a swellable, self-retaining resilient interspinous implant according to claim 1 in the compact first configuration.

24. A swellable, self-retaining resilient interspinous implant which comprises a fluid absorbing polymer which anisotropically expands from a substantially dehydrated compact first configuration having from about 12% to about 30% water by weight of the implant to an expanded second configuration upon absorption of bodily fluid from the surrounding environment, the first configuration being in a state of frozen deformation such that when the implant is in the first configuration the implant includes a first retainer end portion and an oppositely disposed second retainer end portion which are connected by a centrally disposed transverse cross member, the cross member having a smaller cross-section than the end portions, the first and second retainer end portions being dimensioned and configured to frictionally engage respective superior and inferior spinous processes of adjacent vertebrae at their respective outer sagittal faces, the second configuration being dimensioned and configured to fit between, buttress and be frictionally retained in place by the superior and inferior spinous processes, such that when the spinous processes are in a neutral position at least a portion of the implant is compressed slightly by the spinous processes thereby exerting a positive distraction pressure on the spinous processes.

25. A swellable, self-retaining resilient interspinous implant according to claim 24, wherein the expanded second configuration defines a structure having the first retainer end portion and the oppositely disposed second retainer end portion which are connected by the centrally disposed transverse cross member, the cross member being dimensioned and configured such that when in the second configuration, the cross member has a volume that is greater than the space between the two adjacent superior and inferior spinous processes such that when the spinous processes are in a neutral position the cross member is compressed slightly, the first and second retainer end portions being dimensioned and configured to frictionally engage and be retained by the spinous processes at their respective outer sagittal faces when in the second configuration.

26. A swellable, resilient self-retaining interspinous implant according to claim 25, wherein the first retainer end portion has an upper end and a lower end, the second retainer portion has an upper end and a lower end, wherein the respective upper ends and lower ends of the first and second retainer end portions are canted inwardly towards one another.

27. A swellable, resilient self-retaining interspinous implant according to claim 25, further comprising a wear reducing surface which is a durable sheath dimensioned and configured to fit over the cross member.

28. A swellable, resilient self-retaining interspinous implant according to claim 24, further comprising an interiorly disposed support member occupying at least a portion of the interior of the implant.

29. A swellable, resilient self-retaining interspinous implant according to claim 28, wherein the support member extends out of the fluid absorbing polymer.

30. A swellable, resilient self-retaining interspinous implant according to claim 29, wherein the support member includes an exteriorly disposed portion extending out of the fluid absorbing polymer that is adapted and configured to be attached to surrounding tissue and/or bone.

31. A swellable, resilient self-retaining interspinous implant according to claim 28, wherein the support member is selected from the group consisting of fabric, foil and three-dimensional braid.

32. A swellable, resilient self-retaining interspinous implant according to claim 28, further comprising a tether attached to the support member for securing the implant to bone or tissue.

33. A swellable, resilient self-retaining interspinous implant according to claim 24, wherein the fluid absorbing polymer anisotropically expands from the first configuration to the second configuration due to a shape memory property of the polymer.

34. A swellable, resilient self-retaining interspinous implant according to claim 24, wherein the compact first configuration is a rod-shaped configuration.

35. A swellable, resilient self-retaining interspinous implant according to claim 24, wherein the polymer swells upon absorption of fluid and compresses by expression of fluid based upon load applied by the superior and inferior spinous processes.

36. A swellable, resilient self-retaining interspinous implant according to claim 24, further comprising an internal conduit.

37. A swellable, resilient self-retaining interspinous implant according to claim 36, wherein the internal conduit is adapted and configured to receive a guide wire along its length.

38. A swellable, resilient self-retaining interspinous implant according to claim 24, further comprising a tether attached to the implant for securing the implant to bone or tissue.

39. A swellable, resilient self-retaining interspinous implant according to claim 24, wherein the implant further comprises a plurality of layers of fluid absorbing polymer, one or more of the layers having a different modulus of elasticity as compared to another layer.

40. A swellable, resilient self-retaining interspinous implant according to claim 24, wherein the fluid absorbing polymer is a hydrogel.

41. A swellable, resilient self-retaining interspinous implant according to claim 40, wherein the hydrogel is a polyacrylonitrile.

42. A swellable, resilient self-retaining interspinous implant according to claim 24, further comprising a medicinal agent.

43. A swellable, resilient self-retaining interspinous implant according to claim 24, further comprising a wear reducing surface.

44. A swellable, resilient self-retaining interspinous implant according to claim 43, wherein the wear reducing surface is a durable patch dimensioned, configured and positioned on the implant to contact bone thereby reducing wear of the implant caused by contact between the implant and bone.

45. A swellable, resilient self-retaining interspinous implant according to claim 24, wherein the compact first configuration has a three dimensional cone shape.

46. A swellable, resilient self-retaining interspinous implant according to claim 45, wherein the three dimensional cone shape includes a pointed apex.

47. A method of treating a degenerative condition of the spine comprising creating an incision and inserting, through the incision, between two spinous processes of two adjacent vertebrae, a swellable, self-retaining resilient interspinous implant according to claim 24 in the compact first configuration.

48. A swellable, resilient self-retaining interspinous implant which comprises a fluid absorbing polymer which expands from a substantially dehydrated compact first configuration having from about 12% to about 30% water by weight of the implant to an expanded second configuration upon absorption of bodily fluid and which is dimensioned and configured to fit between two spinous processes of adjacent vertebrae, such that when the implant is in the first configuration the implant includes a first retainer end portion having a three dimensional cone shape and an oppositely disposed second retainer end portion which are connected by a centrally disposed transverse cross member, the cross member having a smaller cross-section than the end portions, wherein the end portions are dimensioned and configured to engage the outer sagittal faces of the spinous processes and cooperate to retain the implant between the two spinous processes, and when the implant is in the second expanded configuration the first retainer end portion is expanded, the oppositely disposed second retainer end portion is expanded, the first and second retainer end portions being dimensioned and configured to frictionally engage the spinous processes at their respective outer sagittal faces when in the second configuration.

49. A swellable, resilient self-retaining interspinous implant according to claim 48, wherein the cross member is dimensioned and configured such that when in the second configuration, the cross member has a volume that is greater than the space between the two spinous processes of adjacent vertebrae such that when the spinous processes are in a neutral position the cross member is compressed slightly.

50. A swellable, resilient self-retaining interspinous implant according to claim 48, further comprising an interiorly disposed support member occupying at least a portion of the interior of the implant.

51. A swellable, resilient self-retaining interspinous implant according to claim 50, further comprising a tether attached to the support member for securing the implant to bone or tissue.

52. A swellable, resilient self-retaining interspinous implant according to claim 48, further comprising an internal conduit.

53. A swellable, resilient self-retaining interspinous implant according to claim 48, wherein the three dimensional cone shape includes a pointed apex.

54. A method of treating a degenerative condition of the spine comprising creating an incision and inserting, through the incision, between two spinous processes of two adjacent vertebrae, a swellable, self-retaining resilient interspinous implant according to claim 48 in the compact first configuration.

55. A swellable, resilient self-retaining interspinous implant which comprises a fluid absorbing polymer which expands from a substantially dehydrated compact first configuration having from about 12% to about 30% water by weight of the implant to an expanded second configuration upon absorption of fluid and which is dimensioned and configured to fit between two spinous processes of adjacent vertebrae, such that when the implant is in the first configuration the implant includes a first retainer end portion having a barb shape and an oppositely disposed second retainer end portion which are connected by a centrally disposed transverse cross member, the cross member having a smaller cross-section than the end portions, and when the implant is in the second expanded configuration the first retainer end portion is expanded, the oppositely disposed second retainer end portion is expanded and the centrally disposed transverse cross member is expanded, the first and second retainer end portions being dimensioned and configured to frictionally engage the spinous processes at their respective outer sagittal faces when in the first and second configurations.

56. A swellable, resilient self-retaining interspinous implant according to claim 55, wherein the first retainer end portion is a conical barb.

57. A swellable, resilient self-retaining interspinous implant according to claim 55, further comprising an interiorly disposed support member occupying at least a portion of the interior of the implant.

58. A swellable, resilient self-retaining interspinous implant according to claim 55, further comprising an internal conduit.

59. A swellable, resilient self-retaining interspinous implant according to claim 55, further comprising a tether attached to the implant for securing the implant to bone or tissue.

* * * * *